United States Patent
Scholz

(10) Patent No.: US 9,604,075 B2
(45) Date of Patent: Mar. 28, 2017

(54) METHOD FOR THE OPERATION OF A RADIOTHERAPY SYSTEM AND A RADIOTHERAPY SYSTEM

(71) Applicant: Christian Scholz, Ketsch (DE)

(72) Inventor: Christian Scholz, Ketsch (DE)

(73) Assignee: Siemens Aktiengesellschaft, München (DE)

( * ) Notice: Subject to any disclaimer, the term of this patent is extended or adjusted under 35 U.S.C. 154(b) by 33 days.

(21) Appl. No.: 13/684,463

(22) Filed: Nov. 23, 2012

(65) Prior Publication Data

US 2013/0150646 A1   Jun. 13, 2013

(30) Foreign Application Priority Data

Nov. 23, 2011  (DE) .................. 10 2011 086 930

(51) Int. Cl.
*A61N 5/10* (2006.01)

(52) U.S. Cl.
CPC .......... *A61N 5/1031* (2013.01); *A61N 5/1047* (2013.01)

(58) Field of Classification Search
CPC .... A61N 5/1042; A61N 5/1045; A61N 5/103; A61N 5/1031; A61N 5/1047
USPC ........................................... 600/1, 2; 378/65
See application file for complete search history.

(56) References Cited

U.S. PATENT DOCUMENTS

| | | |
|---|---|---|
| 2005/0116172 A1 | 6/2005 | Trinkaus et al. |
| 2007/0041494 A1 | 2/2007 | Ruchala et al. |
| 2007/0286343 A1* | 12/2007 | Maciunas et al. ............. 378/65 |
| 2008/0240348 A1 | 10/2008 | Kamath et al. |
| 2011/0051893 A1 | 3/2011 | McNutt et al. |

FOREIGN PATENT DOCUMENTS

| | | |
|---|---|---|
| CN | 101120871 A | 2/2008 |
| CN | 101500648 A | 8/2009 |
| CN | 102036712 A | 4/2011 |
| WO | WO2011110958 A1 | 9/2011 |

OTHER PUBLICATIONS

Chinese office Action for related Chinese Application No. 201210475254.X dated Feb. 15, 2016, with English Translation.
S. Kamath et al., "Generalized field-splitting algorithms for optimal IMRT delivery efficiency," Phys. Med. Biol. 52, pp. 5483-5496, 2007.

(Continued)

*Primary Examiner* — Christine H Matthews
*Assistant Examiner* — Joshua D Lannu
(74) *Attorney, Agent, or Firm* — Lempia Summerfield Katz LLC

(57) ABSTRACT

A method for calculating local part radiation doses in a radiotherapy system for applying a total radiation dose in a target volume with several beams is provided. The method includes determining at least one first control plane for controlling the dosing of the beams, determining at least one second control plane for controlling the positioning of the beams, and allocating beams to the first and second control planes. The method also includes, for at least one side of a first control plane, calculating in isolation of the corresponding local part radiation doses of all the beams allocated to the first control plane.

29 Claims, 12 Drawing Sheets

(56) References Cited

OTHER PUBLICATIONS

Y. Li et al., "A novel patch-field design using an optimized grid filter for passively scattered proton beams," Phys. Med. Biol. 52, pp. N265-N275, 2007.
N. Dogan et al., "Automatic feathering of split fields for step-and-shoot intensity modulated radiation therapy," Phys. Med. Biol. 48, pp. 1133-1140, 2003.
S. Kamath et al., "Optimal field splitting for large intensity-modulated fields," Med. Phys. 31(12), pp. 3314-3322, 2004.
E. B. Hug et al., "Fractionated, Three-Dimensional, Planning-Assisted Proton-Radiation Therapy for Orbital Rhabdomyosarcoma: A Novel Technique," Int. J. Radiation Oncology Biol. Phys., vol. 47, No. 4, pp. 979-984, 2000.
Q. Wu et al., "Dynamic splitting of large intensity-modulated fields," Phys. Med. Biol. 45, pp. 1731-1740, 2000.
Y. Liu et al., "Minimizing Total Variation for Field Splitting with Feathering in Intensity-Modulated Radiation Therapy," FAW 2010, LNCS 6213, pp. 65-76.
D. Z. Chen et al. "Optimal Field Splitting, with Applications in Intenstiy-Modulated Radiation Therapy," FAW 2008, LNCS 5059, pp. 4-15.
U. Oelfke et al., "Dose Calculation Algorithms," New Technologies in Radiation Oncology, Heidelberg, pp. 187-196, 2006.
European Search Report dated Apr. 3, 2012 for corresponding Patent Application No. EP 12 188 753.3 with English translation.
D. Z. Chen et al., "A New Algorithm for a Field Splitting Problem in Intensity-Modulated Radiation Therapy," Algorithmica 61, pp. 656-673, 2011.
H. K. Malhotra et al., "Technical and dosimetric considerations in IMRT treatment planning for large target volumes," Journal of Applied Clinical Medical Physics, vol. 6, No. 4, pp. 77-87, 2005.

\* cited by examiner

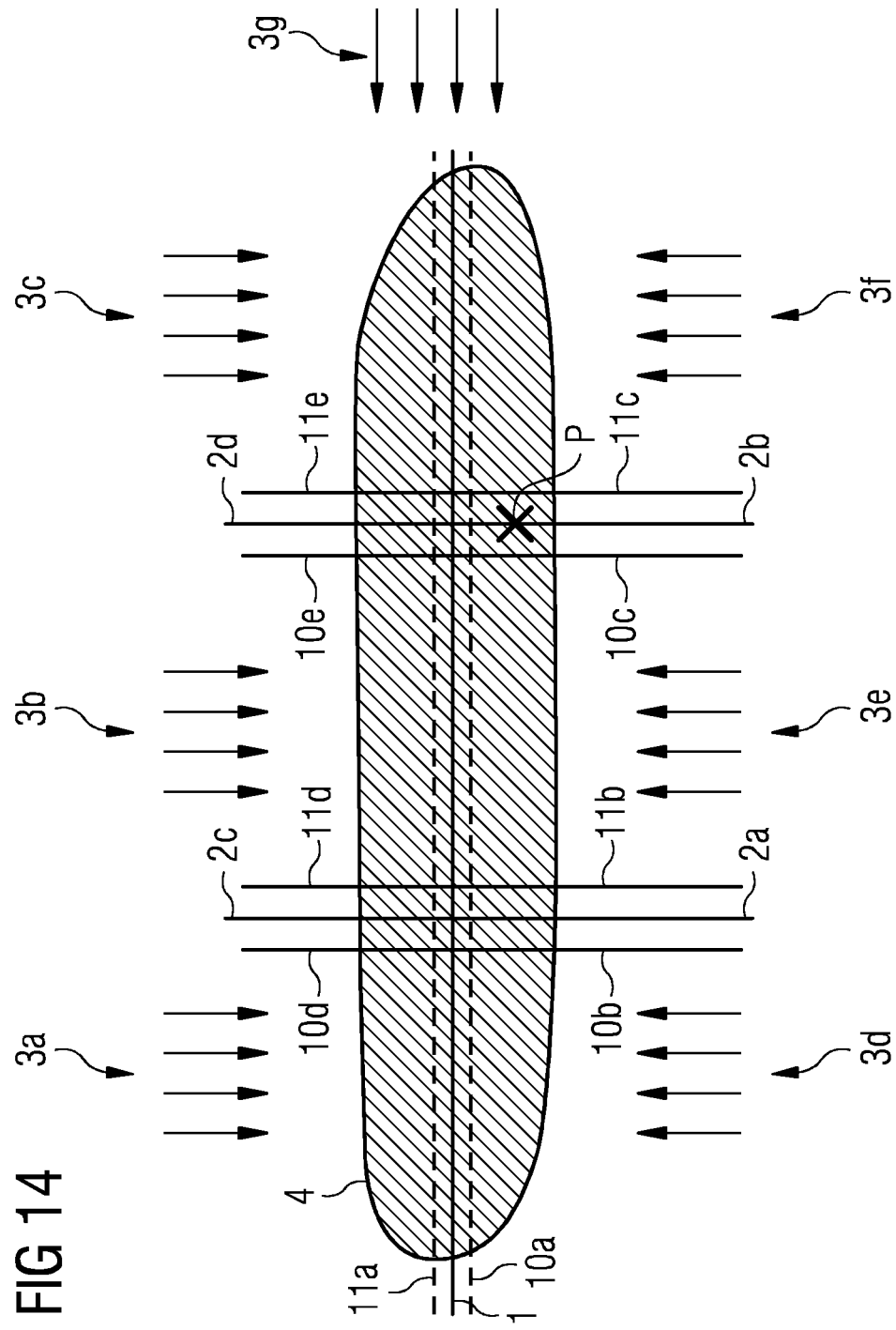

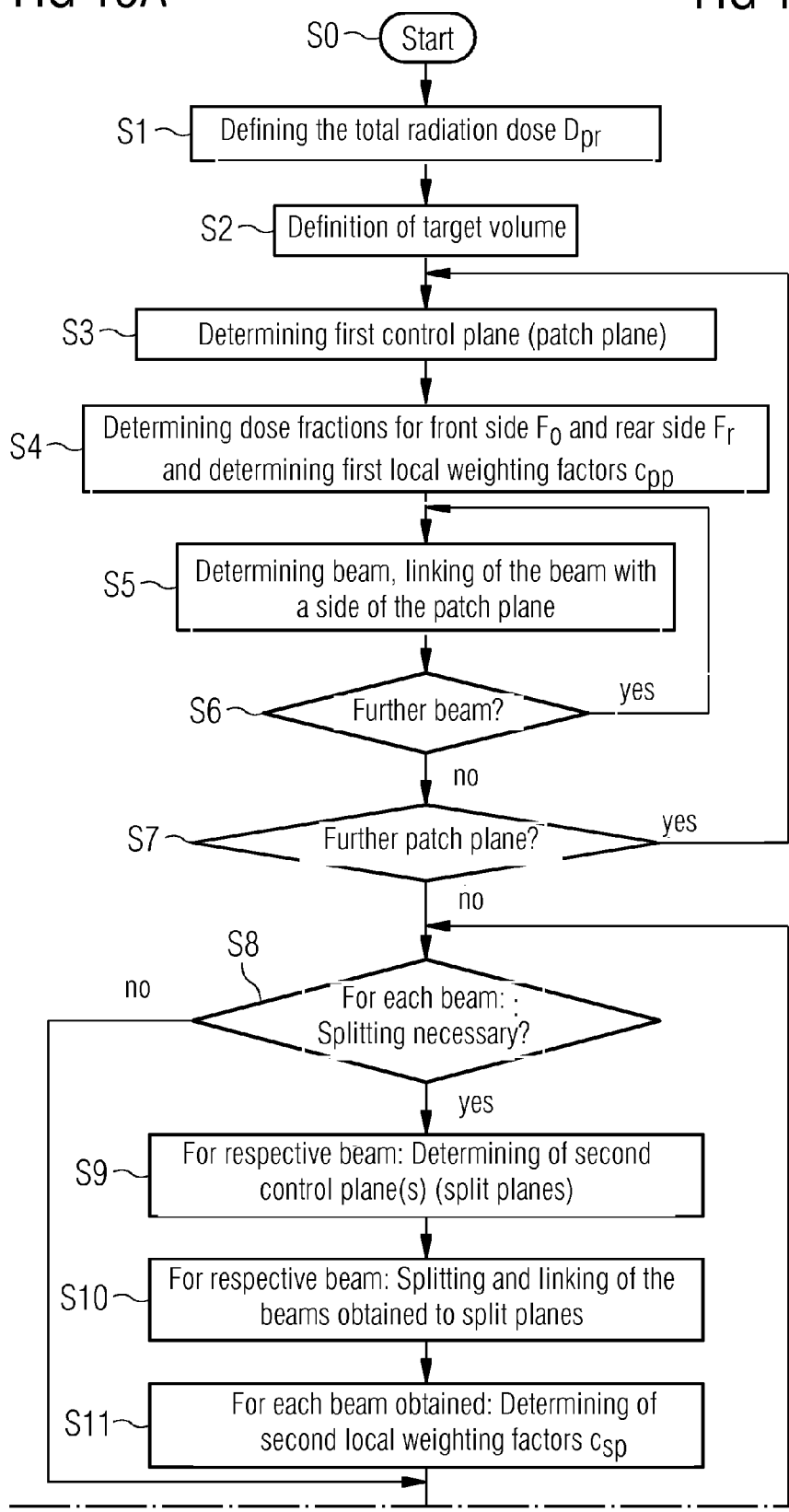

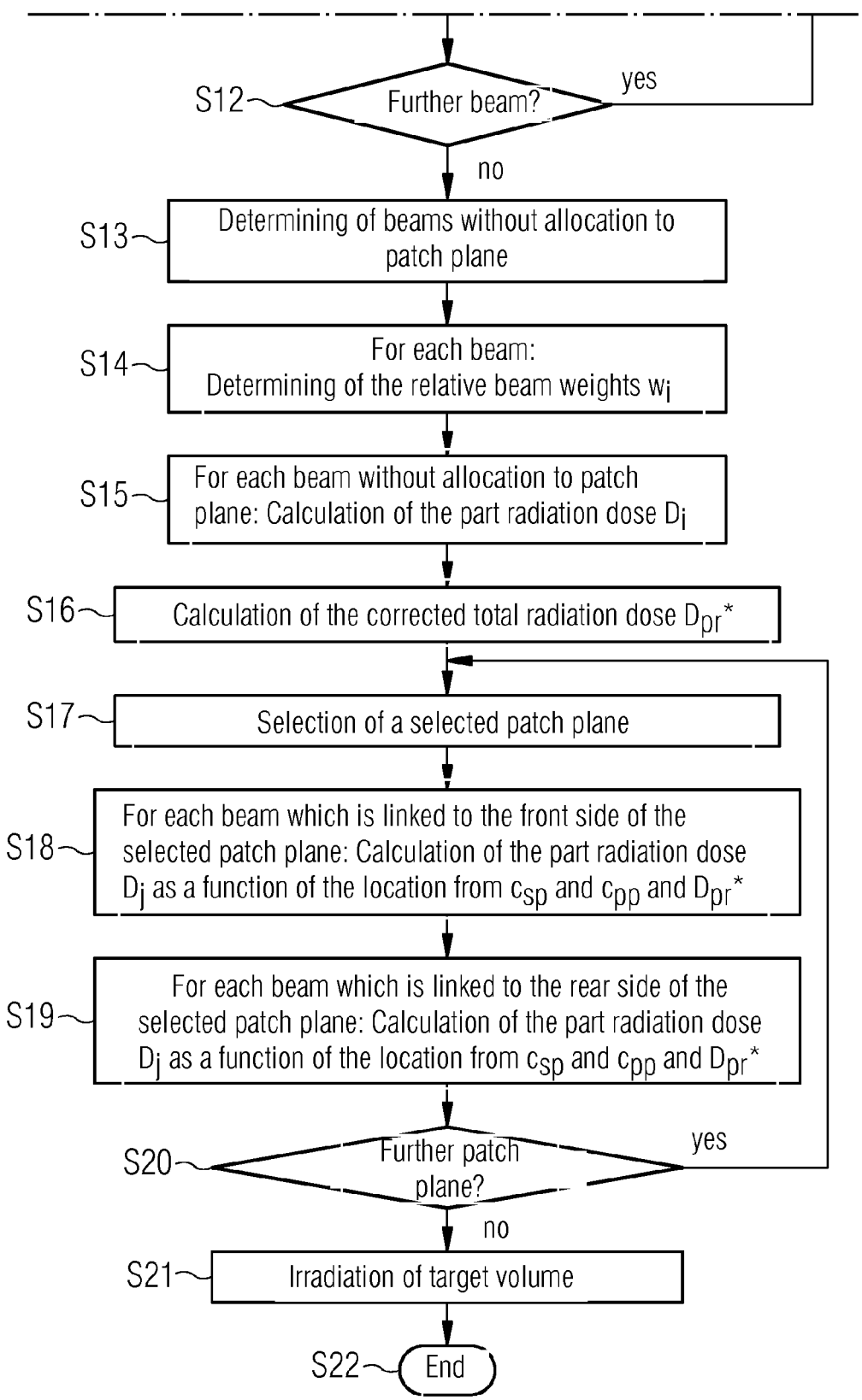

METHOD FOR THE OPERATION OF A RADIOTHERAPY SYSTEM AND A RADIOTHERAPY SYSTEM

This application claims the benefit of DE 10 2011 086 930.1, filed on Nov. 23, 2011, which is hereby incorporated by reference.

BACKGROUND

Radiotherapy (RT) is a therapeutic procedure based on ionizing radiation for the treatment, for example, of cancer. Radiotherapy may, however, also be used for the treatment of other disorders. With radiotherapy, the attempt is made to conduct an adequate therapeutic radiation dose to a diseased area of tissue, while surrounding healthy tissue is spared. The therapeutic effect is based on an ionizing effect of the radiation on diseased tissue.

The dose application by radiation takes place, for example, by intensity-modulated photon therapy (IMRT), protons or carbon ions. A precondition for this is radiation treatment planning based on three-dimensional diagnostics, such as computed tomography or magnetic resonance tomography. In the radiation treatment planning, the radiation parameters are determined such that the necessary total radiation dose is applied in the volume of the tumor or the target volume, and surrounding healthy tissue is spared as may best possibly be achieved. For example, the application of radiation may be carried out by photon radiation in a "Step-and-Shoot" arrangement, in which the beam is switched off while laminations of a laminated collimator move in order by the movement, to define a subsequent beam section. A further arrangement is referred to as the dynamic technique, in which the beam remains switched on while the laminations move. For protons or heavy ions, either "scanned-beam" techniques, in which the beam is scanned in a grid pattern over a target volume, are used, or passive field-shaping techniques are used (e.g., use is made of compensators and energy modulators and range modulators, respectively).

The planning of the radiation treatment of a target volume (e.g., of a tumor) takes place within the framework of a treatment plan. A treatment plan includes, for example, the number and orientation of several different beams that are required for the application of a specific prescribed dose (e.g., a total radiation dose) in the target volume. In each volume element, a beam may apply a part radiation dose. A number of techniques exist in order to vary the applied dose for each volume element.

For dosimetric reasons, more than one beam may be used in order to apply the total radiation dose that has been calculated in relation, for example, to the type of the tumor. For example, the preparation of a treatment plan may include the definition of organs at risk (OAR) that are to be protected from the application of a radiation dose, since OARs react with particular sensitivity to radiation, and major undesirable side-effects are possible in the event of the OAR being irradiated. The radiation treatment may also include the irradiation of several target volumes. For each target volume, the calculation of optimum radiation treatment parameters (e.g., number, type, intensity distribution, and energy of different beams, etc.) is then carried out in an iterative optimization process. Individual parameters from among these may also be predetermined in order to reduce the complexity of the problem.

In certain clinical cases, more extensive methods are provided in order to make possible the treatment of the patient by radiotherapy. Such a case is the situation in which the projection of a target volume in the direction of a beam is greater than the maximum irradiation field of vision of a beam. For example, the maximum field of vision of a beam may be defined by hardware-side limitations. A beam is then to be split into two or more beams. This procedure may be referred to as a "beam split," where the splitting may be achieved, for example, by a "split plane" being defined in order to distinguish on which side of the split plane a specific beam applies a part radiation dose. In the literature, methods that allow for the splitting of a beam are known. For example, Q. Wu et al. disclose in Phys. Med. Biol. 45 (2000) 1731-1740 a method for the splitting of beams.

A further clinical area, in which more extensive methods are provided for the treatment of the patient using radiotherapy, is dosimetric optimization. If a dosimetric advantage is anticipated, it may be advantageous for the target volume to be split into different sub-volumes. The splitting is not necessarily carried out on the basis of hardware limitations, as has been described with regard to the split plane. The different sub-volumes are then irradiated by different beams or several beams in each case. For example, in "scan particle beam therapy," such a splitting of the target volume into sub-volumes is used. This area of application is referred to as the "beam patch," and the corresponding control planes are referred to as patch planes. For example, E. B. Hug et al. disclose in Int. J. Radiat. Onkol. Biol. Phys. 47 (2000) 979, a method of scan proton beam therapy, in which a single beam is moved by scanned magnets into the desired position. Advantages that derive from the use of two proton beams, set in relation to each other by a patch plane are shown for a class of appropriate clinical cases. For example, it is shown that an OAR may be exempted from the application of a dose.

SUMMARY AND DESCRIPTION

The methods discussed above have the disadvantage that it is either possible for split planes to be used or patch planes to be used.

The present embodiments may obviate one or more of the drawbacks or limitations in the related art. For example, a method for the calculation of local part radiation doses in a radiotherapy system that exhibits increased flexibility in treatment planning is provided.

According to one aspect, methods are provided for the calculation of local part radiation doses in a radiotherapy system for the application of a total radiation dose in a target volume with several beams. The method includes determining at least one first control plane for the controlling of the dosing of the beams. Each of the at least one first control plane divides the target volume into two sub-volumes, in each case for the front side and the rear side of each of the at least one first control plane. The method includes allocating at least one beam, and for each control plane, determining a sub-volume total radiation dose for each of the two sub-volumes, as a fraction of the total radiation dose. The method further includes the determination of at least one second control plane for controlling the positioning of the beams, where each of the at least one second control planes subdivides the target volume into two sub-volumes, and the allocation of at least one beam to each of the at least one second control plane. A beam allocated to a second control plane is divided into two by the second control plane in each case, such that the local part-beam dose of the two beams obtained in this way, in different sub-volumes defined by the second control plane, is not equal to zero. The method further includes, for at least one side of a first control plane: Isolated calculation of the corresponding local part-beam doses of all the beams allocated to this first control plane, such that the sum of the local part-beam doses of the beams that are allocated to the side of the respective first control plane that faces the respective sub-volume provides the respective sub-volume total radiation dose, and the sum of the local part radiation doses of the remainder of the beams allocated to the first control planes provides the difference between the respective sub-volume total radiation dose and the total radiation dose.

The term "total radiation dose" provides that dose, defined, for example, in Gray or Sievert units, that is applied within the target volume by one or more beams. The total radiation dose is to lie as close as possible to a prescribed dose that is determined in a radiation treatment plan. For example, a specific total radiation dose may be applied not only by one beam within the target volume, but also by several beams. This may provide dosimetric advantages, as will be explained in greater detail hereinafter.

The target volume may, for example, designate a tumor that it is intended to be destroyed by targeted application of a total radiation dose. To achieve this, beams are used. Beams may designate, for example, X-ray beams, electron beams, heavy ion beams, or even proton beams. Different types of beam are possible, where respective advantages and disadvantages of the different types of beam are known to the person skilled in the art. For example, different beams exhibit different degrees of dependency on the penetration depth of the energy, and on different degrees of biological efficacy.

For example, a connection exists between the energy of the particles (e.g., photons, electrons, protons, heavy ions) and the total radiation dose applied. A beam may be characterized by a "source spot" and a "target spot." The source spot may be defined by a radiation-generating device of the radiotherapy system. The beam direction may be defined by the specification of a beam direction of a beam energy. The middle of a field of vision of a beam is designated as the isocenter.

The term "control plane" designates geometric planes that may be positioned by a user, for example, in a three-dimensional image of a part of a patient's body for controlling the application of radiation dose, for example, within a three-dimensional image of the target area. Control planes may exhibit a thickness. The use of control planes makes it easier for the user to determine specific input parameters in relation to the beams. For example, parameters that relate to the part radiation doses may be easily determined. In addition, parameters that relate to the positioning of the beams may be easily determined. The use of patch planes and split planes may not predetermine the orientation of the beam that is linked to such a plane. For example, several beams may be linked to one side of a patch plane that exhibit different orientations, which provides different beam sources and beam directions.

First and second control planes are, for example, used by a user in order to control both the dosing as well as the positioning of the radiation. First control planes are also designated as patch planes in radiotherapy. First control planes or patch planes may, for example, exert a dosimetric advantage. For example, by the use of patch planes, the situation, in which the total radiation dose is applied by two beams within the target volume, may be achieved. The two beams have different source spots, such that the two beams pass via different routes to the tumor. This has the advantage that surrounding tissue or OARs, which are to receive the smallest possible radiation doses, are protected.

A patch plane divides the target volume into two sub-volumes. A beam may, for example, be linked by a user to one side of the patch plane. Two beams, linked respectively to the front side or the rear side of a patch plane, may exhibit the same isocenter or the same beam source. The user may simultaneously determine a fraction of the total radiation dose that the beam is to apply in the sub-volume that faces the side, with which the beam is linked. For example, the fraction may amount to 70%, which provides that the beam linked to the corresponding side of the patch plane applies 70% of the total radiation dose in the sub-volume. If several beams are linked to the same side of a patch plane, then the beams will divide the given fraction of the total radiation dose; this provides that the sum of all the part radiation doses provides the specified fraction of the total radiation dose or of the sub-volume total radiation dose, respectively.

The sub-volume total radiation dose may be smaller than the total radiation dose. At every point inside the target volume, including inside a sub-volume, the total radiation dose is applied. The difference between the total radiation dose and the sub-volume total radiation dose is applied inside a sub-volume by the beams that are linked to the opposite side of the patch plane. In the numerical example referred to above, in which the sub-volume total radiation dose amounts to a fraction of 70% of the total radiation dose, this would be 30% of the total radiation dose.

Second control planes may be used or determined such that beams that apply a part radiation dose in a target volume that is greater than the maximum volume accessible to the beam are divided in two by a second control plane. Such planes are designated as "split planes." For example, the maximum size of a cross-section through a target volume, which may be scanned by a beam, may be delimited. This may be the case for photon beams when laminated collimators are used, which exhibit a limited field of vision, or for scanned particle beams, with which the field of vision is determined by the maximum controllable deflection of the particle beam from the central beam.

The size of a target volume is not defined by the technical peripheral conditions, however, but, for example, by the size of a tumor, and possibly also by peripheral regions in order for the scattering of the beams to be compensated for in the optimization process, and therefore for a better optimization result to be achieved. If it becomes necessary for a part volume to be irradiated that is larger than the maximum size accessible to a beam, then split planes may be used in order, for example, to divide a beam in two (e.g., a "compound beam"). Two beams are then obtained that, in each case, exhibit a smaller field of vision. A "compound beam" is not a beam that is actually used for irradiation, but is a virtual beam used for calculation during radiation planning.

A beam positioning buffer may also be taken into account within the framework of the target volume, which allows for the individual beams and/or split beams to be displaced.

For example, if the target volume is moved between the application of the first of the two beams and the application of the second of the two beams, or if the beam source is moved, the situation may be reached, in which both beams can apply a part radiation dose in the corresponding target volume.

By the combination of split planes with patch planes, in certain clinical application situations, particularly good results may be achieved in the application of radiation doses in target volumes. Irradiation along the vertebral column is one example. It may be necessary, for example, for the spinal cord to be exempted from the application of a radiation dose. Such areas that are to be protected against the application of a radiation dose are designated as organs at risk (OAR) and may be defined in the treatment planning. By the combination of two essentially opposed beams, which are linked to different sides of a first control plane (e.g., patch plane), the situation may be achieved, in which the organ at risk in the form of the spinal cord is exempted from the application of a radiation dose. It may also be necessary for the irradiation to be carried out along an extended area of the vertebral column. If this target volume exceeds the maximum size of the field of vision of a beam, two control planes (e.g., split planes) are to be used in order to divide the opposed beams into several sub-beams.

According to the present aspect, such an application of beams may be carried out under a combination of first and second control planes. This increases the flexibility in the preparation of a radiation treatment plan. For example, the radiation treatment plan may be prepared such that the undesirable irradiation, or the irradiation of areas that are not involved, will be minimized.

The calculation of the part radiation dose is to be carried out such that different target sizes are maintained. Inasmuch as the calculation is carried out separately for individual sides of a first control plane (e.g., separately and in isolation for the sub-volumes that are facing one side of a patch plane) it may be provided that the sum of all local part radiation doses at each point inside the target volume produces the total radiation dose. This leads to the attainment of the goal of achieving a reliable and effective treatment of the patient. For example, the method according to the aspect presently under discussion allows for the use of several beams that may be respectively allocated to a patch plane and/or a split plane. The calculation of the part radiation doses reacts intuitively to a parameter change by a user such that the part radiation doses are not interfered with by other parameters. Hardware restrictions, such as a maximum field of vision of a beam, may also be taken into account in the calculation of the part radiation doses.

For example, a beam may in each case be allocated unambiguously to a side of a first control plane. This provides that a beam may be allocated to only one side of a first control plane (e.g., a patch plane) and not, for example, to two sides of different patch planes, nor may the beam be allocated to both the front side and the rear side of a patch plane. This unambiguous allocation of beams to one side of a patch plane allows for any ambiguity in the production of a radiation treatment plan or in the calculation of part radiation doses to be avoided.

The local part radiation doses of a beam facing one side of a first control plane may be different in the sub-volumes defined by this first control plane. This provides that, if a beam is allocated, for example, to the front side of a patch plane, the beam applies a specific part radiation dose in the sub-volume facing the front side of the patch plane. For example, this dose may amount to 10 Gray. It may then be advantageous if the beam applies a part radiation dose in the other sub-volume defined by this patch plane (e.g., the sub-volume that faces the rear side of the patch plane, which differs from 10 Gray; 2 Gray).

This may be achieved in that energy values that are determined in the control of the production of the beam are specified such that, depending on the penetration depth of the beam into the tissue (e.g., depending on the position of the beam in relation to the patch plane), different part radiation doses are applied.

The dosimetric effect that results from this, that a beam applies different part radiation doses in different sub-volumes of a patch plane, lies in the fact that it is possible for the radiation exposure of healthy tissue lying, for example, between the skin surface and the target volume to be minimized.

In one embodiment, the first control planes may exhibit a finite thickness, where the beams that exhibit different local part radiation doses on different sides of the respective first control plane provide, using a local course of the local part radiation dose inside the first control plane, a gradual transition of the local part radiation dose.

For example, the position of a first control plane may be defined by the mid-point of the first control plane, if the first control plane (e.g., the patch plane) exhibits a certain thickness. The front side or the rear side, respectively, of a first control plane is then displaced opposite the mid-point (e.g., the position of the first control plane).

In this respect, it may be desirable, if a beam applies different part radiation doses in different sub-volumes, for the transition not to take place instantaneously, as a function of the location, but gradually. This is associated with a dosimetric advantage. It may be possible for local over-increases or weakening of the applied dose (e.g., "hot spots" and "cold spots") to be avoided.

In order to achieve this, it may be of advantage if a gradual transition is provided for the local radiation dose between the front side and rear side of a first control plane or patch plane, respectively, with which a beam is linked. This is because the local part radiation dose in the sub-volume facing the front side and the sub-volume facing the rear side are respectively constant and varied inside the patch plane. The calculation of the local part radiation dose for a sub-volume facing a side of a patch plane then provides that the local partial radiation dose is calculated both outside the patch plane (where, for example, the local partial radiation may be constant) as well as inside the patch plane (where the local partial radiation may change gradually).

Radiation weighting may be determined for each beam, where the radiation weighting factors determine the relative relationships of the part radiation doses of different beams to one another.

The situation may be achieved by radiation weighting, for example, that certain beams apply a greater proportion of a specific sub-volume total radiation dose or of the total radiation dose than other beams. Using radiation weighting, the part radiation doses applied by different beams may be weighted relative to one another.

For example, it may be determined by a weighting factor that a specific first beam applies five times as great a part radiation dose as a specific second beam. The weighting factor for the first beam may, for example, be 5, while the weighting factor for the second beam may, for example, be 1. It is also possible, however, for the weighting factor for the first beam to be 20, and the weighting factor for the second beam to be 4. The ratio of the two weighting factors is 5.

By the use of weighting factors, a dosimetric effect may be achieved. It may be of advantage if a specific beam that exhibits a greater distance interval from an OAR than another beam exhibits a greater part radiation dose than the other beam. The dose applied in the OAR may be minimized.

For example, it may be provided by the method according to the aspect presently under discussion that the radiation weighting factors of the different beams do not influence the calculation of the part radiation doses inside a sub-volume produced by a patch plane. This is the case, because the calculation of the part radiation doses takes place in isolation for a sub-volume that faces one side of a patch plane. If, for example, the radiation weighting factors of a beam that is linked to another side of the patch plane, or to another patch plane, changes within the framework of the treatment planning, then this has no influence on the sub-volume total radiation dose, for which the part radiation dose of a specific beam is calculated. This simplifies the calculation and allows for the part radiation doses to be calculated robustly and by taking the radiation weighting factors into consideration. The part radiation doses may also be flexibly adjusted.

The method may include, inside the target volume for a specific side of a specific first control plane, the determination of first local weighting factors for each distance interval perpendicular to the specific first control plane. The first local weighting factors define the fraction of the respective sub-volume total radiation dose in the total radiation dose. The method includes, for each beam allocated to the specific side of the specific first control plane, the determination of second local weighting factors for each distance interval perpendicular to a second control plane, to which the respective beam is allocated. The second local weighting factors modify the radiation weightings of the beams as a function of the position of the second control plane. The method may include, for each beam allocated to the specific side of the specific first control plane, the calculation of the local part radiation dose for each sub-volume for the respective beam, based on elements selected from the following group: Radiation weighting factors, first local weighting factors, second local weighting factors, and total radiation dose.

The use of first and second local weighting factors may further simplify the calculation of the part radiation doses. For example, using the first local weighting factors, spatially resolved local part radiation doses may be calculated such that, for example, a gradual transition of the local part radiation doses between a front side and a rear side of a patch plane may be provided. To do this, the first local weighting factors are defined as a function of the position in relation to, for example, the mid-point of the first control plane (e.g., perpendicular to the plane defined by the mid-point). It is then possible for a specific calculation to be carried out in each case for each value of a local weighting factor.

The calculation of the part radiation doses may also be simplified by the fact that second local weighting factors allow for a weighting of the radiation weighting factors. For example, the second local weighting factors may modify the radiation weighting factors between 0% and 100% of the value. Such a modification of the radiation weighting factors may take place, for example, multiplicatively. For example, in relation to the second local weighting factors, a gradual transition of the part radiation doses may be calculated in relation to the second control plane (split plane).

For example, the first and second control planes may exhibit a thickness, and the first and second local weighting factors may vary respectively inside the corresponding control plane as a function of the position. In such a way, it may be possible to produce a constant change in the part radiation doses. It is also possible, however, for a step-shaped local change of the part radiation doses to be attained. The calculation of the part radiation doses may be carried out as spatially-resolved for each value of the second local weighting factors. For example, the calculation may be carried out in accordance with the following formula for a side of a first control plane:

$$D_i = \frac{w_i \prod_k c_{sp,ik,k}}{\sum_{j=1}^{n} w_j \prod_i c_{sp,j,l}} c_{pp} D_{pr},$$

where the radiation weighting factors, $c_{pp}$ designate the corresponding spatially-resolved first local weighting factor, $c_{pp}D_{pr}$ outside a patch plane designates the sub-volume total radiation dose, $D_{pr}$ designates the total radiation dose, and $c_{sp}$ designates the spatially-resolved second local weighting factors for all beams that are allocated to the corresponding side of the first control plane.

Specifically, since $c_{pp}$ designates the fraction of the sub-volume total radiation dose in the total radiation dose, it follows that $c_{pp}D_{pr}$ outside a patch plane designates the sub-volume total radiation dose. For a given sub-volume total radiation dose, a calculation of the part radiation doses $D_i$ is then carried out for the different beams that are allocated to the corresponding side of the patch plane. In this situation, $w_i$ designates the weighting factor that belongs to the respective beam. If there are several patch planes present, the factors $c_{pp}$ may be matched to one another. This provides that the sum of all sub-volume total radiation doses at every point inside the target volume is equal to the total radiation dose.

A beam may be allocated to several split planes. The second local weighting factors $c_{sp}$ implement, in each case, a modification of the weighting factors $w_i$ between 100% and 0% of their values (e.g., the second local weighting factors $c_{sp}$ adopt values between 0 and 1). This is attained by multiplication by $0 \leq c_{sp,j,i} \leq 1$. The break in the above formula therefore calculates the proportion of a beam in the sub-volume total radiation dose by norming to the sum of all part radiation dose proportions of all the beams linked to the corresponding side.

From the formula above, it is shown that if, for example, a radiation weighting factor $w_i$ of a beam is altered, which is not linked to the respective side of a patch plane, for which the calculation is carried out in isolation, none of the parameters in the formula above change. Therefore, the calculation does not need to be repeated. This is the case because the calculation is carried out in isolation for the beams allocated to one side of a patch plane (e.g., only the relevant beams are incorporated in the calculation). For example, the weightings of the different beams remain correct in relation to one another. An important consideration for this is the fact that the calculation according to the formula above (e.g., the production of the sum in the denominator) only extends to the beams that are linked to the same side of a patch plane (e.g., of the first control plane).

As a result of the use of the product in relation to the second control factors, overlapping split planes that belong to the same beam may also be determined by calculation from the formula above. In one embodiment, the second control factors $c_{sp}$ adopt values between 0 and 1 in each case in relation to the position with respect to a second control plane. If, for example, the local part radiation dose is calculated for a point inside two local control planes (which may intersect), then several $c_{sp}$-factors may adopt values that are not equal to 0 and not equal to 1. The modification of the radiation weighting factor $w_i$ then takes place accordingly.

For example, the first and second local weighting factors may be defined as spatially resolved in relation to a first and second control plane, respectively, inside the corresponding planes. The part radiation doses may be calculated, spatially resolved as a function of positioning in relation to the control planes for each volume element scanned by the beams. The calculation is carried out in a spatially-resolved manner. The gradual variation of the part radiation doses has already been discussed.

The method may also include the determination of beams without allocation to the first or second control planes. The part radiation doses of the beams are deducted before the isolated calculation of the total radiation dose. Beams that exhibit neither an allocation to a side of a first control plane (e.g., a patch plane) nor to a side of a second control plane (e.g., a split plane) are also designated as normal beams. Such beams apply the part radiation dose, without any dependency on the location, uniformly in the target volume. This makes it possible, before the calculation of the part radiation dose of beams that undergo an allocation to a first or second control plane, to correct the total radiation dose by the sum of the part radiation doses of all the beams that do not exhibit any allocation to control planes. The calculation of the part radiation dose in accordance with the method according to the aspect presently under discussion may be continued accordingly with the corrected total radiation dose.

Such beams may cover a target volume without allocation that is greater than the maximum accessible field of vision. A method for the splitting of these beams may be carried out by split planes. This subordinated splitting is triggered by the superordinated split planes, to which the beam is not allocated.

The method may also include the determination of radiation weighting factors for beams without allocation to first or second control planes, and the adjustment of the total radiation dose for beams that are allocated to first and second control planes based on the radiation weighting factors for beams without allocation to first and second control planes. If radiation weighting factors are also allocated to beams without allocation to control planes (e.g., normal beams), then these beams may have a weighting in relation to the weighting of the beams with allocation to control planes. In this context (e.g., for the calculation of the part radiation dose of a normal beam), the situation may arise where for all the beams allocated to a control plane, an accumulated weighting factor of, for example, 1 or another value, may be determined. If the normal beam has a weighting factor of, for example, 5, then the normal beam exhibits a part radiation dose that is greater by a factor of 5 in relation to the sum of the part radiation dose applied by, for example, beams that are allocated to a first control plane.

According to a further aspect, a method is provided for the calculation of local part radiation doses in a radiotherapy system for the application of a total radiation dose in a target volume with several beams. The method includes the determination of at least one second control plane for controlling the positioning of the beams, where each of the at least one second control planes divides the target volume into two sub-volumes. The method further includes the allocation of at least one beam to each of the at least one second control planes. A beam allocated to a second control plane is divided in two by the respective second control plane such that the local part radiation dose of the two beams obtained in this way is not equal to zero in different sub-volumes, defined by the respective second control plane. The method further includes the determination of beams without allocation to first or second control planes, the correcting of the total radiation dose by subtraction of the local part radiation doses of the beams without allocation from the total radiation dose, and the calculation of the local part radiation dose for all the beams allocated to a second control plane.

Normal beams (e.g., beams without allocation to a first or second control plane) may be combined with a second control plane (e.g., a split plane). As has already been set forth above, before the calculation of the part radiation doses of the beams that are allocated to a second control plane, a correction of the total radiation dose is carried out such that the total radiation dose is corrected by the sum of the part radiation doses of the normal beams.

A radiation weighting may be determined for each beam. The radiation weightings determine the relative relationships of the part radiation dose of different beams to one another. The determination of the beam weights takes place as already explained.

For example, the radiation weighting of all the beams allocated to a second control plane may be in total one. This has already been explained in relation to the further aspects of the present embodiments.

The radiation weighting of the beams that are linked to different sides of a second control plane (e.g., are divided in two by a control plane) is identical. In relation to position precision, the most robust beams possible may thus be obtained.

For example, the sum of all local part radiation doses of all beams at each position inside the target volume may be equal to the total radiation dose. Specifically, if the sum of all part radiation doses is equal to the total radiation dose, then it is provided that an irradiation of the target object (e.g., of the tumor) takes place in accordance with a treatment plan determined beforehand (e.g., in accordance with a prescribed dose). The prescribed dose or the total radiation dose, respectively, is determined in accordance with the clinically required parameters.

The second control planes may exhibit a finite thickness, where beams that are divided in two by a second control plane, by way of a local course of the local part radiation dose inside the second control plane, provide a gradual transition of the local part radiation dose. Effects that may occur with respect to first control planes with finite thickness have already been discussed. Corresponding effects may also occur if second control planes exhibit a finite thickness.

The gradual transition of part radiation doses for beams, which are allocated or linked to a side of a first control plane, a patch plane, has been discussed. A beam may exhibit a part radiation dose that is different on the two sides of a patch plane, but on both sides is not equal to 0. With regard to a second control plane (e.g., with regard to a split plane), however, the local part radiation dose may not be equal to zero only on one side of the split plane.

For example, the local part radiation dose for a beam allocated to a first control plane may not be equal to zero on the different sides of the first control plane, and the local part radiation dose for a beam allocated to a second control plane on precisely one side of the sides of the second control plane may be equal to 0.

This may be the case, since a second control plane (e.g., a split plane) is used if, for example, the field of vision of a beam is not sufficient to cover the whole target volume.

With regard to the gradual transition of the part radiation doses inside a second control plane, this provides that the gradual transition, for example, from a finite value of the local part radiation dose on one side of the split plane to a disappearing value of the local part radiation dose, may take place on the other side of the second control plane.

The beams may be characterized by a beam source. The beam source designates the position, at which the beam is produced. Two beams that are divided in two by a second control plane have, for example, essentially the same beam sources. This is the case, for example, if, during the application of two beams that are divided by a second control plane, the target volume is rotated in relation to the beam source. A displacement or a combination of displacement and rotation of the target volume is possible.

According to a further aspect, a radiotherapy system is provided. The radiotherapy system includes a treatment planning system, a processing device, and a beam generating device. The treatment planning system is configured for the calculation of local part radiation doses for the application of a total radiation dose in a target volume with several beams. The treatment planning system is configured to determine at least one first control plane for controlling the dose administration of the beams. Each of the at least one control plane divides the target volume into two sub-volumes for the front side and rear side of each of the at least one first control plane. The treatment planning system is also configured for the allocation of at least one beam to each first control plane, and the determination of a sub-volume total radiation dose, in each case, for each of the two sub-volumes as a fraction of the total radiation dose. The treatment planning system is configured to determine at least one control plane for the controlling of the positioning of the beams, where each of the at least one second control plane divides the target volume into two sub-volumes. The treatment planning system is also configured for the allocation of at least one beam to each of the at least one second control plane, where a beam allocated to a second control plane is divided into two by the second control plane in each case such that the local part radiation dose of the two beams obtained in this way is in each case not equal to zero in different sub-volumes that are defined by the respective second control plane. The processing device is configured, for at least one side of a first control plane, for isolated calculation of the corresponding part radiation doses of all the beams allocated to the first control plane, such that a sum of the local part radiation doses of the remaining beams allocated to the first control plane provides the difference between the respective sub-volume total radiation dose and the total radiation dose. The radiation generating device is configured such as to apply beams with the part radiation dose calculated by the processing device.

For a radiotherapy system, effects that correspond to the effects that are achieved by the embodiments of the method are achieved.

According to another aspect, a radiotherapy system is provided that includes a treatment planning system, a processing device, and a beam generating device. The treatment planning system is configured for the calculation of the local part radiation dose for the application of a total radiation dose in a target volume with several beams. The treatment planning system is configured to determine at least one second control plane for controlling the positioning of the beams. Each of the at least one second control planes divides the target volume into two sub-volumes. The treatment planning system is also configured for the allocation of at least one beam to each of the at least one second control planes, where a beam allocated to a second control plane is divided in two by the respective second control plane such that the local part radiation dose from the two beams received in this way is, in each case, equal to zero in different sub-volumes defined by the respective second control plane. The treatment planning system is configured to determine beams without allocation to first or second control planes. The processing device is also configured to correct the total radiation dose by subtraction of the local part radiation doses of the beams without allocation of the total radiation dose, and to calculate the local part radiation doses for all the beams allocated to a second control plane. The radiation generating device is configured to apply beams with the local part radiation dose calculated by the processing device.

For a radiotherapy system, effects that correspond to the effects that have been discussed with respect to the other aspects of the present embodiments may be achieved.

BRIEF DESCRIPTION OF THE DRAWINGS

FIG. 14 illustrates an exemplary calculation of the local part radiation dose inside two split planes; and FIGS. 15A-15B represent a flowchart of one embodiment of a method for the operation of a radiotherapy system.

DETAILED DESCRIPTION OF THE DRAWINGS

Figure 1:
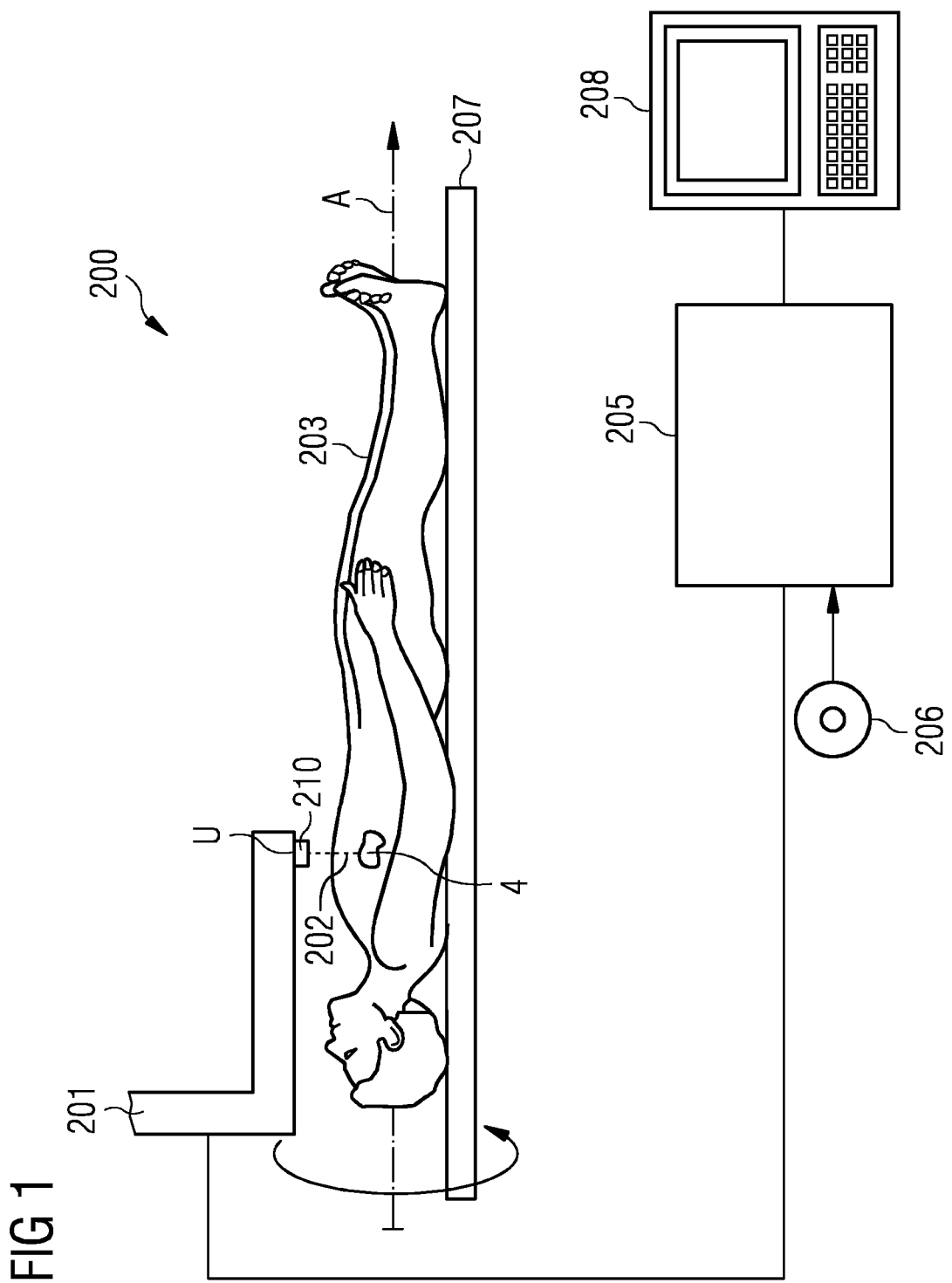
FIG. 1 is a schematic view of one embodiment of a radiotherapy system.

FIG. 1 shows one embodiment of a radiotherapy system 200 that includes a radiation generating device 201. The radiation generating device 201 produces a particle beam 202 or electromagnetic radiation 202 for the treatment of a patient 203 arranged in the radiotherapy system 200. Both particle beams and photon beams or electron beams may be used. Hereafter, however, reference will mainly be made to particle beams, although this should not be interpreted as being limitative.

The patient 203 is arranged along a longitudinal direction that is configured as the axis A. The patient is laid, for example, on a movable and rotatable patient table 207. The beam generating device 201 may include, for example, a linear accelerator (LINAC), or a radiation source, such as, for example, a cobalt-60 radiation source. For example, the radiation generating device 201 may be rotated about the axis A. This makes it possible for the particle beam to be incident on the patient 203 at different beam angles.

The location, at which the beam 202 is generated, is configured as the beam source U. For example, a laminated collimator 210 may be located close to the beam source U. A laminated collimator may include lamellae arranged in several rows that exhibit a high absorption of the beam 202. The lamellae may move individually along an axis that corresponds to an aperture with adjustable form. As a result, the beam 202 may be focused in accordance with the contour of this aperture, and conducted in a targeted manner into a target area inside the patient 203. For example, the contour of the lamellae may be altered during an irradiation procedure. For example, "Intensity Modulated Radiation Therapy" (IMRT), with which both the arrangement of the lamellae is varied over time, and the radiation dose is varied simultaneously, is provided. Different target areas may thus be irradiated with different doses or for complex local dose variations to be achieved. The mode of function of a laminated collimator is known to the person skilled in the art, and further explanation will therefore not be provided here.

For particle beams such as proton or heavy ion beams, the beam may be conducted by active beam guidance 210 via deflection magnetic fields. The beam may be shaped by passive systems, or the energy distribution may be displaced or extended.

In the event of one single positioning of the beam generating device 201, the center of the area that is accessible by the fully opened state of the laminated collimator 210 or by full deflection by deflection magnetic fields of the beam filtering 210 is designated as the isocenter of a beam. Other beam conducting and focusing systems may exhibit differently delimited fields of vision. In other words, the isocenter designates, for example, as the mid-point, the area that is accessible as the maximum by a beam without the movement of the beam generating device 201 (e.g., in the form of rotation about the axis A). In one embodiment, the isocenter is the point in space, about which all isocentric angles rotate: gantry; isocentric table angle; and collimator angle.

In one embodiment, a beam 202 applies in volume elements that have differing distance intervals from the surface of the patient 203, different fractions of the total applied dose. In this situation, there is a penetration depth, at which a maximum dose is applied (e.g., a maximum of the applied dose over the penetration depth). For example, the position of this dose maximum varies as a function of the type of radiation and the energy of the radiation. There is also a certain fraction of the dose applied between the entry of the radiation into the patient 203 and the position of the maximum applied dose. This fraction of the dose may be applied into healthy tissue, such as the skin, and should therefore be minimized. The dependency of the penetration depth and the dose profile on the type of beam 202 and the energy is known to the person skilled in the art and will therefore not be discussed further.

The radiotherapy system 200 further includes a processing device 205 that is coupled to the radiation generating device 201 in order to control the radiation generating device 201. The processing device 205 includes, for example, a microprocessor or a programmable control device that may run a program such as a software package. The program or the software may be loaded into the processing device 205 with the aid of a data carrier 206, for example. The processing device 205 is further coupled to a treatment planning system 208 in order, for example, to receive a specific irradiation plan from the treatment planning system 208.

The treatment planning system 208 may be used to determine a treatment plan. This may take place, as presented hereinafter, although the arrangement may vary slightly from case to case:

1.) Define structure sets for the target volumes and the organs at risk (OAR).
2.a) Define the prescribed doses that are to be applied inside the target volumes.
2.b) Define prescribed doses for organs at risk that are not to be exceeded.
3.a) Define outset plan parameters, definition of the lateral scan raster (e.g., irradiation types, number of beams, isocenters, beam angles, split planes, patch planes, radiation weighting factors, definition of the lateral scan raster, energy distance interval/scan point interval along the depth of the beam).
3.b) Define optimization parameters (e.g., optimization strategy, dose calculation method, resolution of a dose cube such as spatial resolution, with which a beam is rastered, target criterion in order to leave the optimization loop).
4.) Based on the specifications as represented in points 2*a/b*, dose restrictions are defined for the targets and the OAR (e.g., physical restrictions such as minimum and maximum dose restrictions, DVH restrictions, or biological restrictions such as tumor control probability—the probability that the tumor will be destroyed, TCP, normal tissue complication probability—the probability that side-effects will be incurred in normal tissue/organs at risk, NTCP, Equivalent Uniform Dose, the homogeneously radiated dose in a volume that leads to the same biological effect as a non-homogeneous dose distribution in the same volume such as part irradiation of a volume, EUD).
5.) A mostly iterative optimization process is started, where the optimizer attempts to fulfill all the restrictions such as are defined under point 4. A part radiation dose is calculated for different beams, as determined heretofore. A total radiation dose that may be as close as possible to the prescribed dose is obtained as a sum of the part radiation doses. In cases of biological dose distributions, the biological effectiveness of the radiation is to be into account.
6. The result from step 5 is examined, and parameters are, if necessary, altered, and a re-optimization is started. Alternatively, in the event that all the targets were reached, a second independent dose calculation is started, and the plan is used for the treatment of the patient.

Based on the part radiation doses obtained from an irradiation plan (e.g., the dose applied by a beam in a specific volume element), the corresponding dose restrictions may be automatically adjusted for every location before the optimization is started.

Within the framework of the preparation of a treatment plan, split planes and patch planes may be produced for controlling the treatment of the patient by the treatment planning system 208. This is explained in greater detail below.

In the event that the target projection in the beam direction exceeds the maximum irradiation field range, the original beam is split into two or more sub-beams with different isocenters or target points. This may be referred to as "beam split," and the splitting may take place by a split plane being defined by the treatment planning system 208 in order to differentiate on which side which beam should apply which dose.

If a dosimetric advantage is being expected, the target surface may be split into two different sections, where one or more beams irradiate one section, and where other beams irradiate the second section. This is the case, for example, for scanned particle radiation treatment (e.g., using protons or heavy ions). There may also be an application field for other irradiation circumstances. This application field is referred to as the "beam patch," and the surfaces are designated by patch planes.

If either a split plane or a patch plane is defined by the treatment planning system 208, both these cases have in common the fact that the target volume is divided into several sub-volumes, in which the beams apply specific doses. These two cases also have in common that, in order to maximize the robustness of the radiation plan against patient movement or organ movement, an intensity ramp for each beam is defined between the split planes and the patch planes as a transition from one target plane to an adjacent target plane.

There are, however, a number of differences between split beams (e.g., split plane) and patched beams (e.g., patch plane). Split beams are used when geometric beam restrictions are infringed such as, for example, the maximum field size and beam form that are imposed by equipment limitations. In the case of split beams, the isocenter is to be displaced for each split beam in order to compensate for these restrictions.

Patch beams, by contrast, may be used in order to achieve better dose distribution in relation to the situation without patch planes. For example, two opposed particle beams may be used. A patch plane will then reduce the dose at each beam input significantly, so that normal tissue may be exempted from too great a dose application. A further example is the situation, in which an organ at risk is at least partially surrounded by the target. Patch planes may significantly reduce the dose that is applied to the organ at risk, because the beams do not cross through the organ at risk. Accordingly, beams that are linked to patch planes may share the same isocenter, even if, in some cases, advantages are derived if several isocenters are used.

Split beams (e.g., beams linked to a split plane) also do not deposit any dose in target volumes that lie beyond the split plane. The intensities beyond the split plane are zero. This is provided in order to fulfill the restriction of the maximum field size for each beam. By contrast, this restriction is not required for patch beams. In this case, the user may define, using treatment planning system 208, a residual dose level for the surface, with which the patch beam is not linked.

In one embodiment, using the treatment planning system 208, beam weights of beams may be determined in order to control the dose contribution of each beam. By contrast, the dose in a sub-volume defined by a patch plane is fixed and is not changed by beam weights. Otherwise, the user would acquire the possibility of changing the part radiation dose of a beam by two parameters (e.g., using the patch plane and using the beam weighting). The desired part radiation dose is therefore changed during the optimization of the beam weighting.

For example, using the treatment planning system 208, both split planes and patch planes may be defined simultaneously. There are clinical cases in which this is good practice. For example, this is the case if radiation is to be applied along the length of the vertebral column. In this situation, the spinal cord is the organ at risk that may be exempted from dose application by the use of two patch beams, offset by 90° against one another. Despite this, the target surface is too large for the target surface to be acquired by one single beam. Accordingly, the patch beams are to be further split by a split plane.

A further clinical case, in which the combination of split beams and patch beams is good practice, is a gradual transition of the dose between immediately adjacent regions of a target volume that are to be irradiated under different circumstances or with different parameter sets. Where overlapping beams and corresponding dose ramps are used in this surface, potential local deviations from the desired dose (e.g., "hot spots" and "cold spots") that are incurred by imprecisions during the treatment set-up may be avoided.

Figure 2:
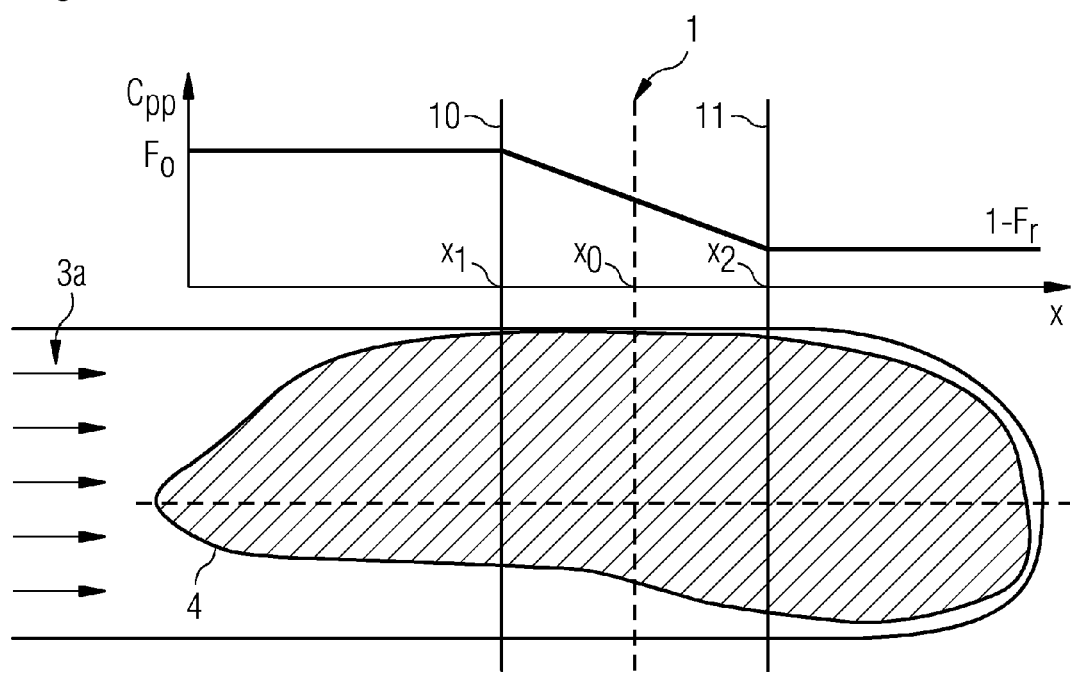
FIG. 2 is a cross-section of an exemplary patch plane with an incident beam.

In order to explain in greater detail the differences between a split plane and a patch plane, these two situations are considered in isolation in the following FIGS. 2 and 3. In FIG. 2, for example, a particle beam 3a is incident from the left on a target volume 4 (represented as hatched area). For example, the particle beam 3a may come from a radiation source (not shown) with a small location co-ordinate x through the patient to the target volume 4. The target volume 4 may, for example, be a tumor. The target volume 4 may also have a depth perpendicular to the plane of the drawing in FIG. 2 (not represented).

For example, there may be a specific position $x_0$ inside the target volume. It is desired that a specific total radiation dose ($D_{pr}$) be applied inside the target volume 4. The total radiation dose may be obtained from a radiation plan, such as discussed in relation to FIG. 1. By the appropriate selection of the particle energy, as explained heretofore in relation to FIG. 1, the situation that a beam, as a function of the position x, applies a specific dose along the section represented in FIG. 2 may be achieved.

In FIG. 2, a patch plane 1 is placed, for example, by a treatment planning system, as explained heretofore in relation to FIG. 1, at a specific position $x_0$ along the cross-section represented in FIG. 2, inside the target volume 4. The patch plane 1 exhibits a specific thickness in the direction x. This thickness is limited by a front side 10 and a rear side 11 of the patch plane 1.

There are a number of reasons why it may be advantageous to use a patch plane 1 in the example from FIG. 2. One possibility is that the target volume 4 is located deep inside the patient. If the prescribed total radiation dose is applied by, for example, only one beam inside the target volume 4, this has the consequence that a large dose is applied between the patient's skin surface and the target volume 4 on a path of the one beam. This is the case because, as already described in relation to FIG. 1, a fraction of the dose applied inside a specific volume is also applied on the way to this volume, by a beam. For example, the fraction of the dose is applied on the way to the target volume (e.g., with $x<x_0$ in healthy tissue) and is therefore to be minimized. One possibility for minimizing this dose is to use two beams instead of one. The two beams may have different beam sources (e.g., opposed sources) and accordingly pass on different paths through the patient to the target volume 4. Only a small fraction of the dose will then be applied along the respective beam paths.

In FIG. 2, the patch plane 1 is located at the position $x=x_0$. The patch beam 3a is linked to the front side 10 of the patch plane 1, and in FIG. 2, passes from the left into the target volume 4. A further patch beam is not graphically indicated but may, for example, pass from the opposite side, in FIG. 2 from the right, to the target volume 4.

For example, using a treatment planning systems 208, a sub-volume total radiation dose may be allocated to the patch plane 1 or, respectively, to the patch beam 3a. The sub-volume total radiation dose $D_o$ is defined by a fraction $F_o$ of the total radiation dose $D_{pr}$ in the sub-volume facing one of the two sides of a patch plane. In the example from FIG. 2, the left side of the sub-volume 4 (e.g., the side with $x<x_1$ (facing the front side 10 of the patch plane 1)) is associated with a sub-volume total radiation dose that results in $$D_o = F_o D_{pr}.$$

The total radiation dose $D_{pr}$ is still always applied inside this sub-volume for $x<x_1$. This is not effected by the patch beam 3a alone, however (this applies the sub-volume total radiation dose $D_o$), but by further beams that are allocated, for example, to the rear side 11 of the patch plane 1. The further beams then apply the missing fraction $(1-F_o)D_{pr}$ of the total radiation dose $D_{pr}$.

In this situation, the sub-volume total radiation dose $D_o$ or $D_r$ are calculated in each case from the prescribed total radiation dose $D_{pr}$ by multiplication by the front side or rear side dose fraction respectively, $F_o$ or $F_r$, which is determined in the treatment plan:

$$D_{o/r} = F_{o/r} D_{pr}.$$

In this situation, the respective sub-volume total radiation dose $D_o$ or $D_r$ is the dose that is applied by a beam or a number of beams that are linked to the side of the patch plane facing the respective sub-volume.

In one embodiment, the respective part radiation dose applied along the direction x (e.g., the beam direction of the particle beam 3a in FIG. 2) is calculated for different points.

$$D_i = c_{pp} \frac{w_i}{\sum_{j=1}^{n} w_j} D_{pr}; \; 1 - F_{o/r} \leq c_{pp} \leq F_{o/r}.$$

n designates the number of the beams linked to the same side, in the case above, with the front side 10 of the patch plane 1.

The factor $c_{pp}$ is a first local weighting factor that designates the local fraction of the total radiation dose $D_{pr}$.

The first local direction factors $c_{pp}$ differ in this situation, for example, in the sub-volumes facing the different sides of the patch plane and inside the patch plane also as a function of the location x. For example, inside the patch plane, as is represented in FIG. 2, a gradual transition in the locally applied dose may be attained by a gradual transition of the first local direction factors $c_{pp}$.

In the case of the exemplary embodiment represented in FIG. 2, one beam is linked to the front side 10 (e.g., n=1). In other embodiments, however, n>1 may be selected. This may be of advantage if different beam sources are desired for beams that are linked to the same side of a patch plane.

$w_i$ represents radiation weighting factors. The radiation weighting factors $w_i$ define the relative contribution from different beams to the sub-volume total radiation dose.

For example, different beams may be provided with different radiation weighting factors $w_i$ that apply only a specific fraction of the sub-volume total radiation dose, according to the respective radiation weighting factors. For example, with several different beams linked to a specific side of a patch plane, different doses may be allocated to different beams, and accordingly, the dose applied in healthy tissue on the way to the target volume may be dosimetrically optimized. Accordingly, all beams that are linked to one side of the patch plane contribute to the respective sub-volume total radiation dose $D_o$ and $D_r$. The radiation weighting shows, by weighting factors $w_i$, the anticipated effect on the dose distribution (e.g., the beam weights contribute relatively only to the linked side of the patch plane).

In the event of the summation from equation 2 being extended over all the beams that are linked to the target volume 4, the respective sub-volume total radiation dose $D_o$ and $D_r$ would be modified by the beam weights $w_i$. This is not desirable.

The first local weighting factor $c_{pp}$ may be any function as a dependency of the relative distance interval from a patch plane. The gradual transition represented in FIG. 1, in the form of an intensity ramp, may be relevant for specific clinical applications.

For example, in the event that both patch planes and split planes are present, equation 2 is to be generalized. This is explained hereinafter. In the first instance, however, in FIG. 3 following, the case of the split planes is discussed in isolation.

Figure 3:
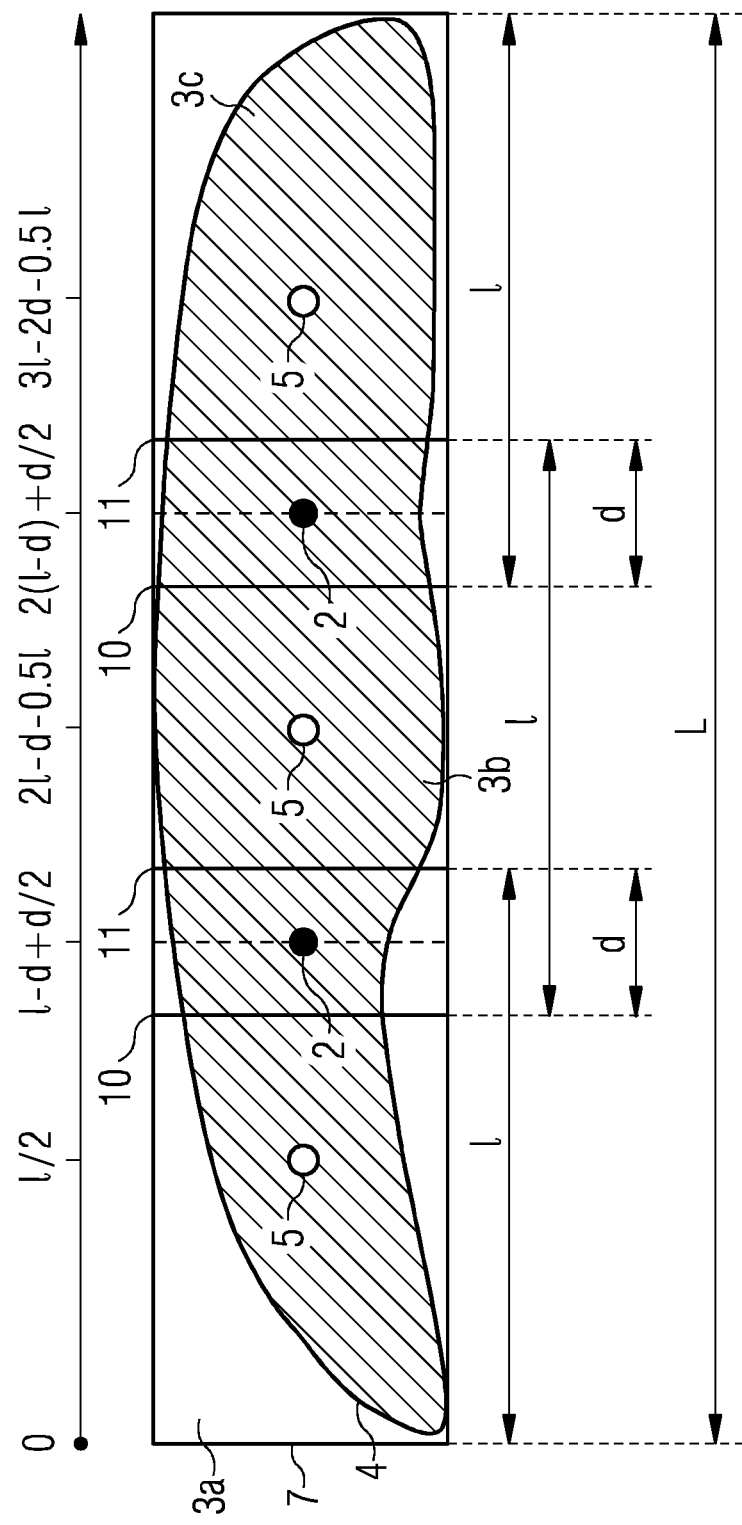
FIG. 3 is a view from above of two exemplary split planes with three incident beams.

With regard to FIG. 3, an exemplary embodiment, with which only split planes are used in order to provide the application of a total radiation capacity in a target volume, is described. For example, in specific clinical cases, the desired target volume or, respectively, the beam that is desired may be greater than may be supplied with respect to the hardware. Accordingly, the beam (e.g., the "split beam") is to be split into several sub-beams and, for example, the patient is to be moved between the different beam processes of the different sub-beams. The sub-beams may overlap to a specific user-definable degree in order to avoid local deviations from the prescribed total dose in the transition areas, due, for example, to imprecisions in the positioning of the patient (e.g., "hot spots" and "cold spots").

A splitting strategy for beams is demonstrated with reference to FIG. 3 by way of example in the case of a one-dimensional splitting of the beam. The splitting of the beam may also take place in other directions and, respectively, with multiple splitting in different directions (e.g., at any desired angle to the split plane represented in FIG. 3), as well as inside the plane of the drawing represented in FIG. 3 (e.g., also perpendicular to the plane of the drawing).

L designates the length of a section plane through the target volume. The target volume designates, for example, the size of a tumor and optionally, a surrounding positioning buffer (e.g., "expansion margins"). Inside the positioning buffer, beams and, for example, split planes may be placed. As a result of this, the dose conformity may be increased in the tumor.

The maximum length accessible by a beam is designated by $l_{max}$, and the length of the overlapping between two adjacent beams is designated by d. As a further assumption, $l_{max} > D$ and $L > l_{max}$. $l_i$ is the resultant length of a beam i, where $l_i$ is always smaller than $l_{max}$. The maximum beam length $L_{max}$ that may be obtained from the combination of n beams is then $$L_{max} = n \cdot l_{max} - (n-1) \cdot d.$$

Accordingly, the number of beams used in order to apply the dose uniformly on the target is $$n = \left\lceil \frac{L-d}{l_{max} - d} \right\rceil.$$

Here, the operator ⌈ ⌉ designates the rounding up (e.g., the "ceiling" function). L may not assume precisely such values that precisely n beams of the length $l_{max}$ will fit with overlapping of precisely d into the length L. Accordingly, the position of the beam isocenters may be varied and optimized accordingly. In order to provide that the different beams do not exhibit too markedly different sizes, or that one beam is not very small, and the remaining beams service a very large target volume, the size $l_i$ of the beams I may be uniformly calculated as $$l_i \equiv const_{\forall i} = l = \frac{L + (n-1)d}{n}; \text{ where } l \leq l_{max},$$

Inasmuch as the left side of this equation may be used as a source, the isocenter of each beam may be calculated based on this, relative to the source, as $$x_i = (i+0.5)l - id; 0 \leq n \leq 1.$$

While in the foregoing case a specific arrangement of the target volume in the co-ordinate system was selected, other arrangements are nevertheless also possible. A position vector may then be added at the start of the target volume.

The position $s_j$ of each split plane j may be calculated, based on this, as $$s_j = j(l-d) + \frac{d}{2}; 1 \leq j \leq n-1.$$

These equations are defined such that the numbering of the beams begins with i=0. By contrast, the numbering of the split planes begins with =1.

A co-ordinate inside the respective split plane is designated as a size x, while, by contrast, the co-ordinate x in the exemplary embodiment from FIG. 2 (e.g., patch plane) is designated a co-ordinate perpendicular to the respective patch plane.

As shown in FIG. 3, this may result, for example, in a specific target volume 4 being irradiated by three beams 3a, 3b, 3c. In FIG. 3, the beams are oriented perpendicular to the plane of the figure. The target volume 4 in the exemplary embodiment in FIG. 3 is so large that, due to the hardware limitations, a single beam may not apply the dose uniformly over this target volume (e.g., a cross-section of the target volume). A possible hardware limitation is, for example, the maximum opening of the lamella filter or the maximum possible deflection of a particle beam, as described with reference to FIG. 1. The maximum field of vision 7 of the beams is represented in FIG. 3 by dotted lines. The size of the target volume L is, for example, greater than $l_{max}$, as a result of which the beam may be split by split planes. The irradiation or application of the dose, respectively, may be carried in three stages by three beams 3a, 3b, 3c. In the interim, either the target volume 4 is to be moved such that the different beams may reach different areas of the target volume, or the beam generating device is to be moved accordingly in relation to the target volume. In the example from FIG. 3, three beams 3a, 3b, 3c are used in order, respectively, to apply a total dose. The isocenters 5 of the different beams exhibit equal distance intervals from each other. This is attained by the calculation described heretofore. It is not necessary, with regard to patch planes, that different beams that are linked respectively to a patch plane are to exhibit different isocenters. The positions of the two split planes are marked by the centers 2. The first split plane is located at the co-ordinate 1−d+d/2, and the second split plane is located at the co-ordinate 2(l−d)+d/2.

As further shown from FIG. 3, the two split planes exhibit a finite thickness d. The split planes are delimited by front sides 10 and rear sides 11. For example, as described hereinafter with reference to FIG. 4, inside the thickness of a split plane, a gradual course of the different applied part radiation doses $D_i$ is provided. As a result, local deviations from the total radiation dose $D_{pr}$ may be prevented. Such deviations may occur, for example, due to imprecise positioning between the application of two beams. This is discussed in greater detail with reference to FIG. 4.

Figure 4:
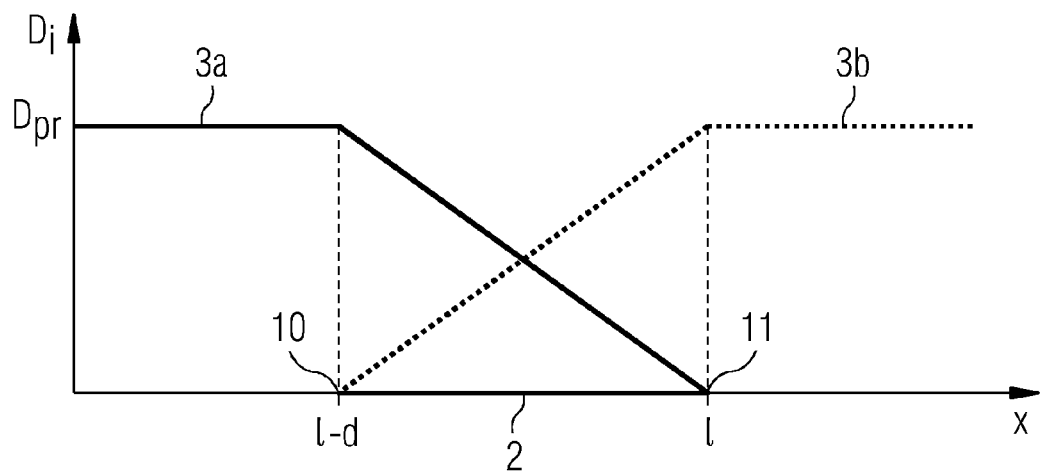
FIG. 4 illustrates a gradual variation of an exemplary part radiation dose inside a split plane.

FIG. 4 shows, using a linear local course of the part radiation dose $D_i$ of the two beams 3a and 3b, in every area (e.g., for all positions x), the total radiation dose $D_{pr}$ is applied, and local deviations from the total radiation dose $D_{pr}$ may be avoided. The part radiation dose $D_i$ of the beam 3a in the area between x=l−d and x=l varies gradually from the maximum part radiation dose, in the case of FIG. 4, $D_i=D_{pr}$ to the minimum value of the dose (e.g., $D_i=0$). This may be attained by linear interpolation. For the beams 3a and 3b, this provides $$D_1 = \begin{cases} D_{pr} & ; x \leq l - d \\ 0 & ; x > l \\ D_{pr} - \frac{D_{pr}}{d}(x - l + d) & ; x \in [l-d, l] \end{cases} \text{ and}$$

$$D_2 = \begin{cases} D_{pr} & ; x > l \\ 0 & ; x \leq l - d \\ D_{pr} - D_1 & ; x \in [l-d, l] \end{cases},$$

where $D_1$ designates the part radiation dose of the beam 3a, and $D_2$ designates the part radiation dose of the beam 3b. These two equations may be reformulated such that local weighting factors $c_{sp,1}$ and $c_{sp,2}$ are obtained for the two beams 3a and 3b in relation to the split plane. This then gives $$D_1 = c_{sp,1} \cdot D_{pr}$$

$$D_2 = c_{sp,2} \cdot D_{pr}. \quad (1)$$

These equations may be applied directly to every dose calculation method, inasmuch as a linear dependency pertains between the radiated intensities and the applied doses. For conventional treatment planning with photons, electrons, and other particles with constant radiobiological effectiveness, this precondition is fulfilled. For every non-linear dependency between intensity and applied dose, such as is the case, for example, for the biological dose of heavy ions, the $c_{sp}$ factors may be adjusted in order to take the biological effectiveness of a beam into consideration.

Figure 5:
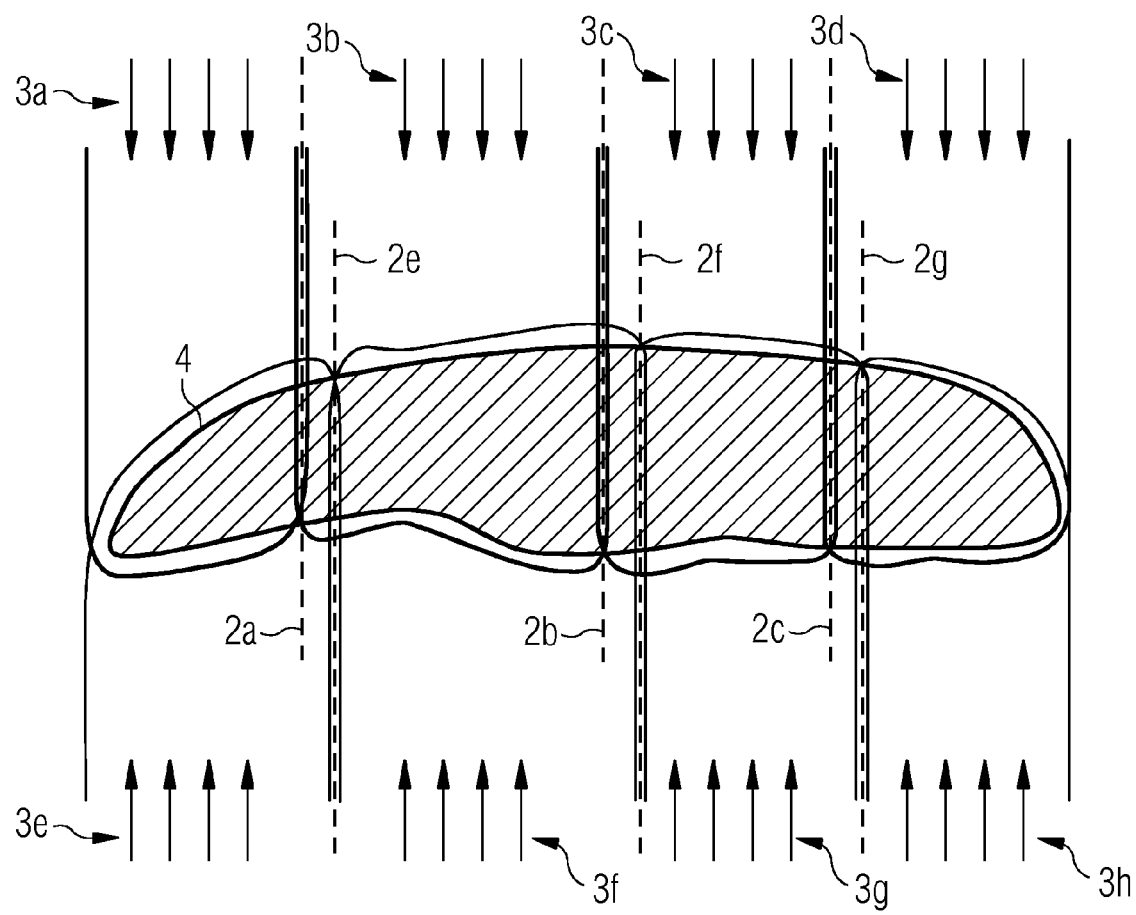
FIG. 5 is a cross-section of six exemplary split planes.

Explanations have been provided with reference to the exemplary embodiments represented in FIG. 3 and FIG. 4, regarding the arrangement and dosage of beams that are linked by a split plane. For example, in FIG. 3 (e.g., in contrast to FIG. 2), a view from above of the two split planes 2 is represented. This provides that the orientation of the beams in FIG. 3 is oriented into the plane of the figure or out of the plane of the figure. By contrast, the orientation of the beam in FIG. 2 is inside the plane of the drawing. Such a case is also represented in FIG. 5, in which a case is described hereinafter in which six split planes 2a-2g that control the positioning and dose administration of a total of eight beams 3a-3h are present. As shown in FIG. 5, four beams 3a to 3d in FIG. 5 are incident from above on the target volume 4 (represented by broken lines). A further four beams 3e to 3h, as represented in FIG. 5, are incident from below on the target volume 4. The beams 3a to 3d incident from above are positioned by the split planes 2a to 2c, while the beams 3e to 3h are positioned by the split planes 2e to 2g. For example, the split planes 2a and 2e have different positions along the target volume. This is possible, because the split planes 2a to 2c for the beams 3a to 3d may be determined entirely independently of the split planes 2e to 2g for the beams 3e to 3h (e.g., the treatment planning system from FIG. 1). In the entire target volume 4, the same total radiation dose $D_{pr}$ is applied overall. This is done by an addition of the part radiation doses $D_i$ of the different beams.

For the situation in which two beams are incident on a target volume from different directions, a splitting is to be carried out by split planes. This splitting is carried out independently of one another for the two beams. Accordingly, two (split) beams are linked with one split plane when the splitting is carried out only in one direction (e.g., one dimensional). In the case of two-dimensional beam splitting for large target volumes, the number of beams linked by one split plane may increase. For example, that split planes that belong to different original beams (e.g., non-split beams) will overlap.

Figure 6:
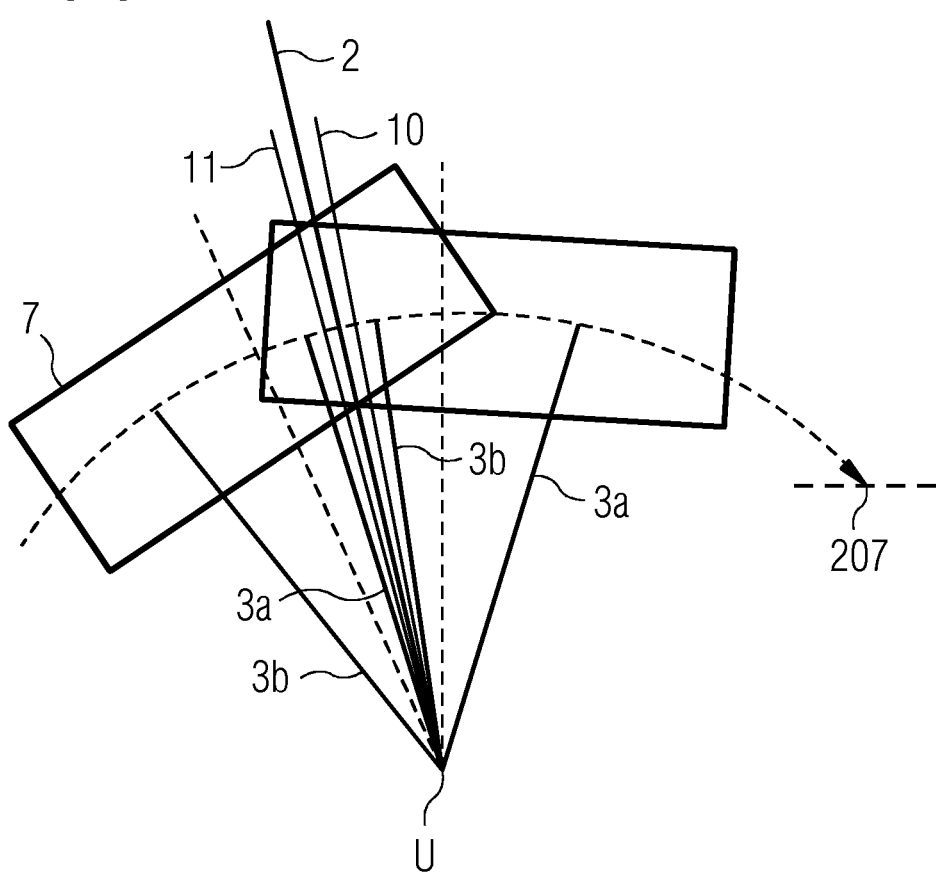
FIG. 6 shows the rotation of a patient table between the application of two divergent beams with an exemplary split plane.
Figure 7:
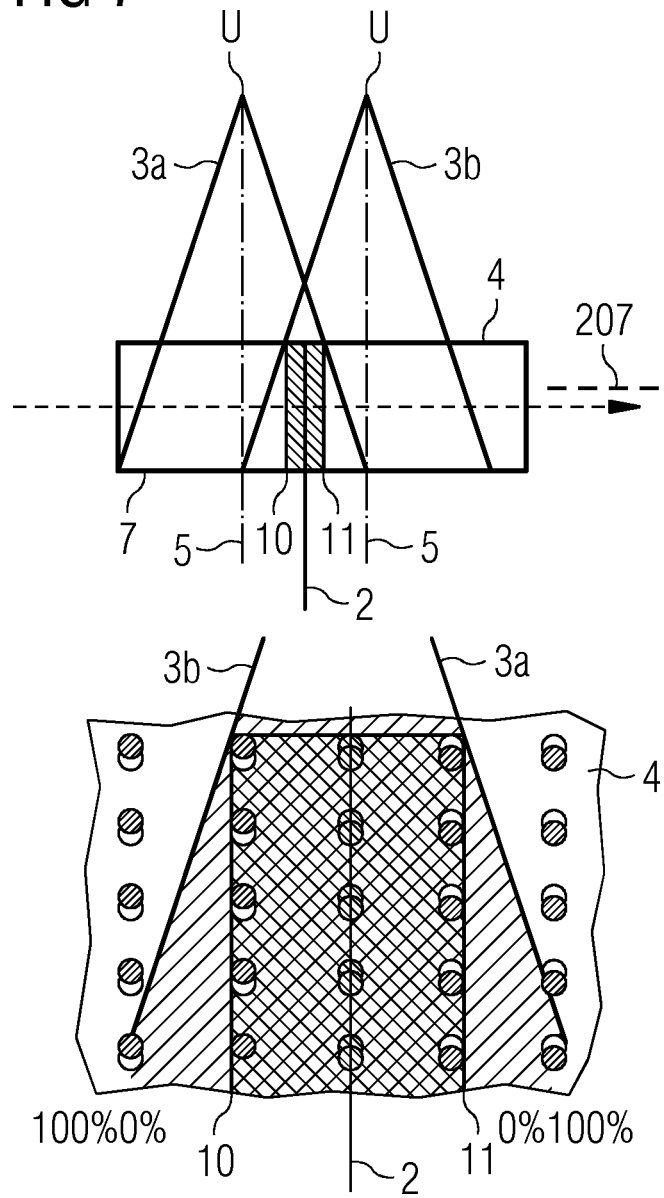
FIG. 7 shows the translation of a patient table between the application of two divergent beams with an exemplary split plane.

It is explained in greater detail hereinafter, by reference to the exemplary embodiments shown in FIG. 6 and FIG. 7, how the positioning may take place between the sequential use of two beams separated, for example, by a split plane. In FIG. 6, an embodiment, in which a patient table 207 is rotated in relation to the beam source U, is represented. By contrast, an embodiment represented in FIG. 7, in which the table 207 is moved in relation to the beam source U, is provided. As shown in FIG. 6, upon a rotation of the table 207 about the beam source, the irradiation of a target volume takes place from the same beam source U. By contrast, if the table 207 is moved in relation to the beam source U, the beam source U appears, from the reference co-ordinate system of the table 207, from two different positions. This is shown in FIG. 7. Both in FIG. 6 and FIG. 7, two beams 3a and 3b are used for the applying of a dose in a target volume. In both cases, a split plane 2 is present. The split plane 2 has a front side 10 and a rear side 11. The front side and the rear side 10, 11 delimit an overlapping region that is represented by broken lines in FIGS. 6 and 7.

If the patient table is moved between the application of two beams, this may have the following effect: Every collision check in a radiation plan (see FIG. 1) is to be repeated in order to provide that no radiation dose passes into organs at risk, for example. This may result in a beam that in a previous collision check was found to be usable being rejected after the movement of the patient table.

For diverging beams (e.g., beams of which the diameter increases as the distance interval from the beam source U increases), the movement of the table has the consequence that, as well as a lateral translation of the table, a rotation, tilting, or turning of the table is also possible. This is represented in greater detail in FIG. 6. For example, in the case of especially divergent beams (e.g., the source to target distance (FID) is very small), the rotating of the table 207 may compensate for the beam divergence. The rotation of the table is represented by a broken line. Two beams 3a and 3b are used to apply a dose inside a target volume. For example, the beams exhibit an overlap. The size of the overlap increases as the distance interval to the beam source U increases, which is due to the divergence of the two beams. A split plane 2 is located inside this overlap area. The split plane 2 is characterized by a front side 10 and a rear side 11.

By the rotation of the table, the beam divergence may be compensated for. Specifically, due to the rotation of the table, the overlapping area becomes larger as a function of the increasing distance from the beam source U. This provides, over the depth of a target volume, that the overlapping of the beams is sufficient to provide, inside a split plane 2, a gradual transition of the beams 3a and 3b.

If the overlapping between the beams through the depth of the target volume is equal to or greater than the thickness of the split plane, the movement of the table between the use of two sequential beams linked by a split plane may also take place in the form of a translation. In this case, no tilting or turning of the table is necessary. Such a case is shown in FIG. 7. In FIG. 7, top, the use of two beams 3a and 3b is shown one after the other. The table 207 was moved between the use of the two beams 3a and 3b. Accordingly, the beams 3a and 3b in FIG. 7, top, have different beam sources U. The beams 3a and 3b exhibit a high divergence due, for example, to a small distance interval to the beam source U. This provides that over the depth of the target volume 4, the diameter of the beam changes. If a split plane 2 is now located inside the target volume 4, characterized by a front side 10 and a rear side 11, where one beam 3a is linked to the front side 10 and a further beam 3b is linked to the rear side, then the thickness of the split plane does not exceed the minimum overlapping of the two beams 3a and 3b. This provides, for example, that the thickness of the split plane 2 is restricted by the point that is closest to the beam source U. This is shown enlarged in FIG. 7, bottom, where the thickness of the split plane 2 inside a target volume 4 lies inside the overlap between the two beams 3a and 3b. Inside the thickness of the split plane (e.g., between the front side 10 and the rear side 11 of the split plane 2), a gradual transition of the part radiation doses that belong to the two beams 3a and 3b is provided. As shown in FIG. 7, bottom, on the left side of the split plane 2, the beam 3a delivers 100% of the total radiation dose (and the beam 3b 0% of the total radiation dose), while this is precisely the other way round on the right side of the split plane 2.

As long as the beam overlap is large enough to cover the entire split plane inside the target volume (e.g., the beam target points are to be capable of being positioned in the case of a scanned particle beam inside the entire split plane for both beams), good optimization results may be achieved.

A case is discussed hereinafter, in relation to FIG. 8, in which a radiotherapy system may not provide intensities of a particle beam 3a, 3b that are as small as may be desired. This is relevant, for example, if, as discussed in relation to FIGS. 3 and 4, a transition between the dose applied by a particle beam, between a maximum and a minimum value, is used over the layer thickness of a split plane 2. In one embodiment, there may be a linear connection between applied doses and intensities of the beams. The radiobiological effect of a beam of known intensity is to be known in some cases in order to be able to allocate a dose. A radiotherapy system exhibits a minimum limit of the beam intensity. This may be designated as $I_{min}$. If two beams with intensity profiles of $I_1$ and $I_2$ are taken into consideration, then, if either $I_1$ or $I_2$ become smaller than $I_{min}$, the intensity distribution is to be adjusted, so that all intensities are greater than $I_{min}$, or some of the intensities are equal to zero. The latter is only the case if $I_0$ is smaller than $2I_{min}$, which does not apply in clinical cases, as a result of which this option may be disregarded in this context. If Imin is particularly small, this intensity correction may not be required.

Figure 8:
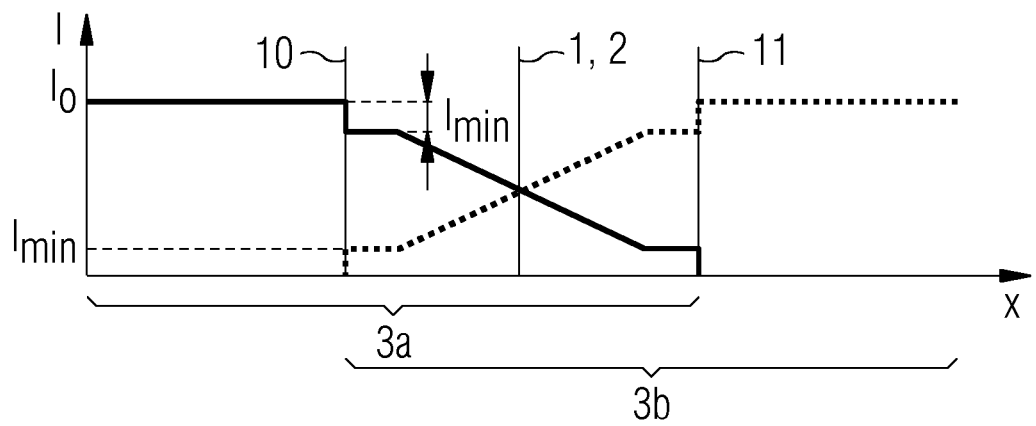
FIG. 8 shows the gradual variation of a beam intensity inside an exemplary split plane, taking account of a minimum applicable beam intensity.

The transition between the locally applied part radiation dose of two beams (e.g., inside a split plane 2; between a front side 10 and a rear side 11) or also inside a patch plane 1 is represented in FIG. 8, where a minimum intensity $I_{min}$ was taken into consideration. Due to the fact that this dose distribution is easily changed due to the intensity change, a recalculation of the treatment plan is to be carried out.

Figure 9:
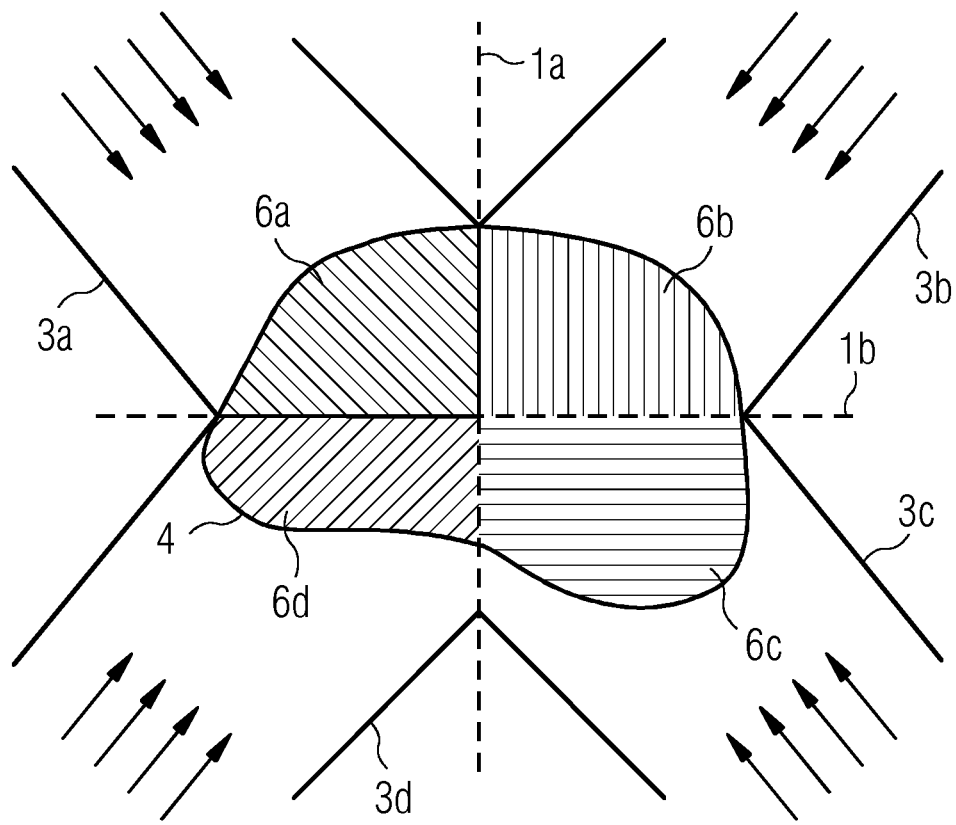
FIG. 9 illustrates the allocation of four beams to two exemplary patch planes.

With regard to FIG. 9, a case is considered, in which two patch planes 1a and 1b exist. In the event of a beam being allocated to more than one patch plane, the complexity of the allocation of the correct beam to the correct side of one of the respective patch planes may increase for the user. The system (e.g., the treatment planning system from FIG. 1) may support the process of the allocation of a beam to a side of a patch plane. It may then be advantageous, for example, to provide, using an appropriate user interface, that the user may select, instead of sides of a particular patch plane, a corresponding sub-volume. This is illustrated with reference to FIG. 9. The two patch planes 1a and 1b divide the target volume 4 into four sub-volumes 6a to 6d. It is then difficult for the user to allocate the different beams 3a to 3d to the corresponding sides of the different patch planes. It is easier if the user does not have to select a side (e.g., the front or rear side) of a specific patch plane for the linking of the beam, but, accordingly, only one of the different sub-volumes 6a to 6d. The system may automatically carry out the allocation to the different front and rear sides of the different patch planes 1a and 1b. The corresponding arrangement may also be extended for a 3D problematic situation.

In FIGS. 2 to 9, cases were discussed, in which either patch planes or split planes were used in order to control the positioning and dose administration of particle beams. Such cases may be used as part of an exemplary embodiment according to the present embodiments. Hereinafter a case will be discussed making reference to FIG. 1, in which the treatment planning system 208 is configured such that a combination of split planes and patch planes is used. For example, the processing device 205 is then configured so as to calculate correctly the individual part radiation doses $D_i$ of the different beams that are linked respectively to patch planes or split planes. "Calculate correctly" may be that it is provided, at each point inside a target volume 4, that the part radiation dose applied by all the beams is equal to the total radiation dose $D_{pr}$. This may take place by taking account of radiation weighting factors $w_i$, such as have been explained, for example, with reference to FIG. 2. This further takes place by the use of first and second local weighting factors $c_{pp}$ and $c_{sp,i}$ that define the respective part radiation doses as a function of the positioning in relation to either patch planes or split planes.

For split planes, the part radiation dose $D_i$, making reference, for example, to the description of FIG. 5 results in $$D_i = \frac{w_i \prod_k c_{sp,i,k}}{\sum_{j=1}^{n} w_j \prod_l c_{sp,j,l}} D_{pr} \text{ where } 0 \leq c_{sp,j/j} \leq 1.$$

n relates to the total number of all beams that it is intended to irradiate the target volume. The $c_{sp}$ (e.g., the second local weighting factors) are derived from Equation 1. Only beams that contribute a dose at a specific point in relation to the split planes are taken into account. The product extends over all second local weighting factors $c_{sp}$ of the split planes, with which the beam under consideration is linked. In this way, the overlapping of split planes, to which the same beam is allocated, may also be taken into account.

If both split planes and patch planes are now used in the same treatment plan, the following equation is used:

$$D_i = \frac{w_i \prod_k c_{sp,i,k}}{\sum_{j=1}^{n} w_j \prod_l c_{sp,j,l}} c_{pp} D_{pr}. \tag{2}$$

The second local weighting factors (e.g., the $c_{sp}$, factors of the split planes) are used to weight the radiation weighting factors $w_i$. This is the case because the different second local weighting factors $c_{sp}$ may assume values between 0 and 1. For example, the calculation from Equation 2 only extends over the n beams that are allocated to a specific patch plane side, for which the first local weighting factor $c_{pp}$ is defined.

Due to the fact that the calculation of the different radiation doses is carried out in isolation for an individual side of a patch plane (e.g., only for a first radiation weighting factor $c_{pp}$), in each sub-volume defined by a patch plane, the corresponding sub-volume total radiation dose $D_o$ or $D_r$, respectively, will be fulfilled. As a result, by addition of the different sub-volume total radiation doses (e.g., the sub-volume total radiation doses that are applied by beams that are linked to opposing sides of a patch plane), the total radiation dose $D_{pr}$ is provided.

For example, the first and second local weighting factors $c_{pp}$ and $c_{sp}$ are not used identically. In other words, no equation is used in the form $$D_i = \frac{w_j \prod_k c_{i,k}}{\sum_{j=1}^{n} w_j \prod_l c_{j,l}} D_{pr}, \tag{3}$$

$c_{i,k}$ corresponds to the factors $c_{sp}$ and $c_{pp}$. Such an equation 3 is mathematically correctly formulated, but it has the disadvantage that the sub-volume total radiation doses $D_o$ and $D_r$ are no longer constant because the respective part radiation doses $D_i$ are also dependent on the radiation weights $w_i$.

Figure 10:
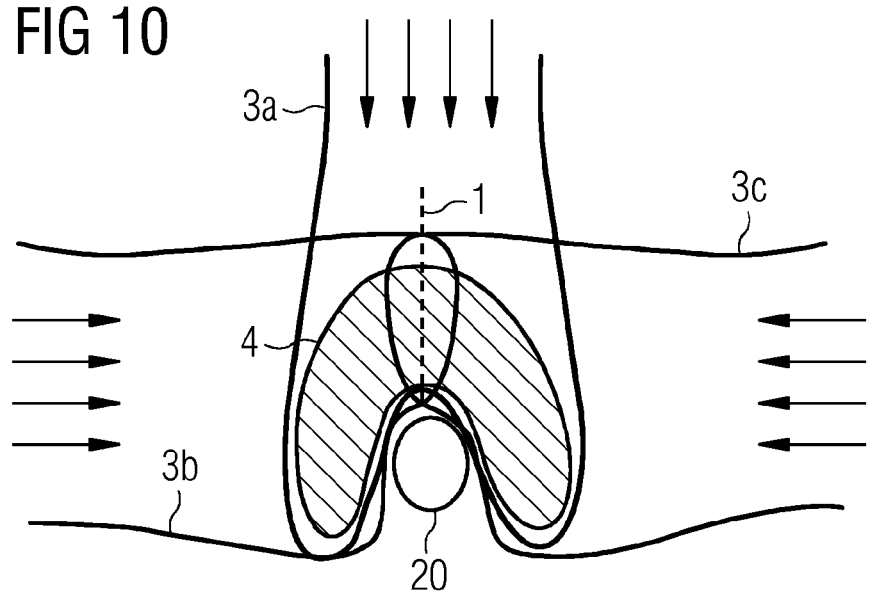
FIG. 10 illustrates the allocation of two beams to an exemplary patch plane, where one beam is present without allocation to a patch plane.

Beams that are not defined with a patch plane or a split plane may be defined. This is discussed in greater detail hereinafter on the basis of FIG. 10. In FIG. 10, a case is represented, in which two beams 3b and 3c are linked to a patch plane 1. The beams 3b and 3c reach the target volume 4 from opposite directions (in FIG. 10 from the left and right sides). A beam 3a that is not linked to the patch plane 1 is present. The beam 3a is also not linked to a split plane. Such a configuration of beams 3a to 3c may be used if the target volume 4 is located close to an organ at risk 20. In this situation, it may, for example, be worth seeking to establish that no or only a low dose is applied inside the organ 20, while a large dose is applied inside the target area 4.

One embodiment for determining the radiation weighting factors $w_i$, both for the beams 3b and 3c linked to the patch plane 1 and also for the beam 3a that is not linked to the patch plane such that the total radiation dose is fulfilled in accordance with the radiological specifications, is for the beam weights of all the beams linked to the patch plane 1 to be set as equal to 1. In this sense, the total radiation dose $D_{pr}$ is in the first instance divided between the beams that are neither linked to a patch plane nor a split plane and the remaining beams. For example, a dose $D_{pr,pp}$ may be allocated to the patch plane in FIG. 10, which is given as $$D_{pr,pp} = \frac{1}{1 + \sum_{m} w_m} D_{pr}.$$

It is also possible, however, for a weighting other than 1 to be allocated to the patch plane. In this case, the equation given above now becomes:

$$D_{pr,pp} = \frac{1}{w_{pp} + \sum_{m} w_m} D_{pr}.$$

Equation 2 above, which represents the part radiation dose for a beam that is allocated both to a patch plane as well as to a split plane, may be reformulated accordingly:

$$D'_j = \frac{w_j \prod_k c_{sp,i,k}}{\sum_{j=1}^{n} w_j \prod_l c_{sp,j,l}} c_{pp} D_{pr,pp}. \quad (4)$$

The total radiation dose $D_{pr}$ has been adjusted. The adjusted total radiation dose $D_{pr,pp}$ is corrected by the amount that is applied by beams that are allocated neither to a patch plane nor a split plane. A part radiation dose may be allocated according to such beams:

$$D_q = \frac{w_q}{1 + \sum_{m} w_m} D_{pr}, \text{ respectively} \quad (5)$$

$$D_q = \frac{w_q}{w_{pp} + \sum_{m} w_m} D_{pr}.$$

With regard to FIG. 10, a numerical example is to be taken into account by way of illustration. To do this, the total radiation dose should amount to $D_{pr}$=60 Gray, and the beam weights $w_i$ should be: For beam 3a: $w_1$=5; for beam 3b: $w_2$=2; and for beam 3c: $w_3$=3.

For example, the beam 3b is allocated to the front side of the patch plane 1 (left side in FIG. 10). This side of the patch plane is characterized in that a dose fraction of $F_o$=70% is allocated, and a rear side dose fraction of $F_r$=80% is allocated. This provides that a beam 3b linked to the front side of the patch plane 1 applies a sub-volume total radiation dose $D_o$ of 70% of the total radiation dose $D_{pr,pp}$ (e.g., corrected by the part radiation dose applied by the beam 3a) into the sub-volume facing the front side of the patch plane. If Equation 5 is taken into consideration, then the dose $D_1$ applied by the beam 3a is given by $$D_1 = \frac{5}{1+5} 60 Gy = 50 Gy.$$

The part radiation dose applied by the beams 3b and 3c may be calculated. This takes place separately and in isolation for the front side and the rear side of the patch plane 1. In the first instance, the total radiation dose $D_{pr,pp}$ corrected by the part radiation dose applied by beam 3a is calculated. Equation 4 is used for this, and the following is obtained:

$$D_{pr,pp} = \frac{1}{1+5} 60 Gy = 10 Gy.$$

It is then further possible for the part radiation doses $D_{2,o}$ and $D_{3,o}$ to be calculated, which designate, respectively, the part radiation doses of the beams 3b and 3c in the sub-volume allocated to the front side of the patch plane 1 (on the left side in FIG. 10). The corresponding part radiation dose may also be calculated for the two beams 3b and 3c in the sub-volume facing the rear side of the patch plane 1 (on the right side in FIG. 10):

$$\left.\begin{aligned} D_{2,o} &= \frac{2}{2} \cdot 0.7 \cdot 10 Gy = 7 Gy \\ D_{3,o} &= \frac{2}{2} \cdot 0.3 \cdot 10 Gy = 3 Gy \end{aligned}\right\} = D_{pr,pp}$$

$$\left.\begin{aligned} D_{2,r} &= \frac{3}{3} \cdot 0.2 \cdot 10 Gy = 2 Gy \\ D_{3,r} &= \frac{3}{3} \cdot 0.8 \cdot 10 Gy = 8 Gy \end{aligned}\right\} = D_{pr,pp}.$$

The rotated numerical example above is only of an illustrative nature. The different parameters for the different beams may be adjusted in numerical value.

In the numerical example from FIG. 10 the total radiation dose $D_{pr}$=60 Gray is distributed onto the different beams such that beam 3a applies 50 Gray inside the target volume. In FIG. 10, on the left side of the patch plane 1 (e.g., in the sub-volume that faces the front side of the patch plane 1), the beam 3b applies 7 Gray, and the beam 3c applies 3 Gray. The sum of the sub-volume part radiation dose applied by the beams 3b and 3c results in 10 Gray. These 10 Gray are the missing 10 Gray that, in sum with the 50 Gray of the part radiation dose applied by beam 3a, come to the total radiation dose of 60 Gray. In the sub-volume represented on the right side in FIG. 10 (e.g., the sub-volume that faces the rear side of the patch plane 1), the ratio of the part radiation dose applied by the beams 3b and 3c is different. Specifically, the beam 3b applies a part radiation dose of 2 Gray, and the beam 3c applies a part radiation dose of 8 Gray. The total radiation dose is equal to 60 Gray.

Figure 11:
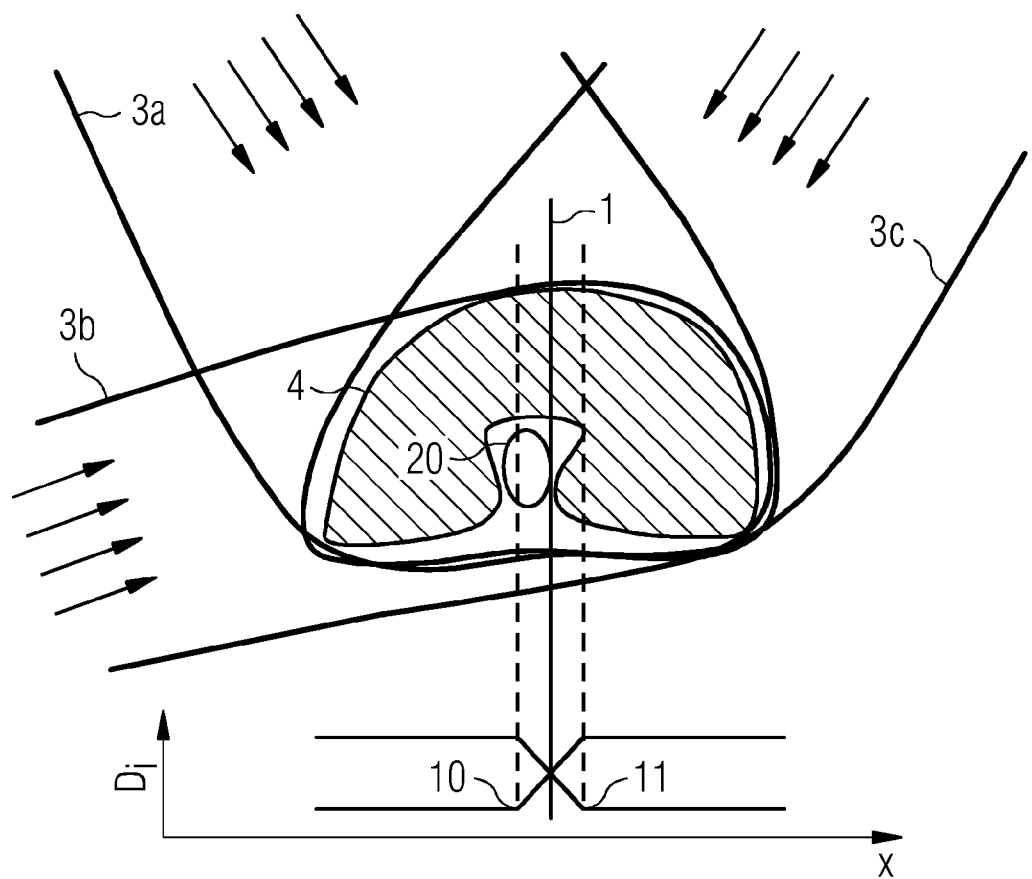
FIG. 11 illustrates the allocation of three beams to an exemplary patch plane, where the patch plane exhibits a thickness.

In FIG. 11, an exemplary embodiment that is similar to the exemplary embodiment from FIG. 10 is described. Once again, a patch plane 1 is present. In the exemplary embodiment from FIG. 11, the patch plane exhibits a finite thickness, in contrast to the exemplary embodiment from FIG. 10. The front side 10 is represented in FIG. 11 on the left side, while the rear side 11 of the patch plane 1 is represented on the right side. By contrast with the exemplary embodiment from FIG. 10, the exemplary embodiment from FIG. 11 does not exhibit any beams that are not allocated to the patch plane 1. For example, the beams 3a and 3b are allocated to the front side of the patch plane 1, and the beam 3c is allocated to the rear side of the patch plane. All three beams have different beam sources. For example, beam 3a in FIG. 11 falls into the target volume 4 from the top left. By contrast, the beam 3b, which is also linked to the front side 10 of the patch plane 1, comes in FIG. 11 from the left lower side into the target volume 4. It is now possible, making use of the foregoing equations, to calculate the respective part radiation doses for the different beams. For example, that the calculation of the part radiation doses for the beams 3a and 3b takes place separately from the calculation of the part radiation dose for the beam 3c is taken into account. This is the case, since the calculation is carried out in isolation for one side of a patch plane, and specifically only for those beams that are allocated to this side of the patch plane. In the case of FIG. 11, for example, the beams 3a and 3b are allocated to the front side (e.g., the left side) of the patch plane 1.

By way of example, for the total radiation dose $D_{pr}=60$ Gray and the beam weights $w_1=5$ (beam 3a), $w_2=2$ (beam 3b), $w_3=3$ (beam 3c) is to be carried out. The dose fractions allocated to the patch plane amount to $F_o=70\%$ for the sub-volume facing the front side and $F_r=80\%$ for the sub-volume facing the rear side. This provides that the beams that are linked to the front side of the patch plane apply 70% of the total radiation dose in this sub-volume (e.g., the sub-volume facing the front side of the patch plane 1 (the left side sub-volume in FIG. 11)). By contrast, the beams that are allocated to the rear side 11 of the patch plane 1, in the rear-side sub-volume (e.g., right side sub-volume in FIG. 11), apply 80% of the total radiation dose. The respective missing 30% (e.g., front side) and 20% (e.g., rear side) of the sub-volume total radiation dose are applied by the beams respectively linked to the opposite side of the patch planes (e.g., in the exemplary embodiment in FIG. 11) in the sub-volume facing the front side 10 of the patch plane, 20% of the total radiation dose is applied by the beam 3c, and 30% of the total radiation dose in the sub-volume of the patch plane 1 facing the rear side 11 is applied by the beams 3a and 3b.

The calculation according to the foregoing Equation 2 then gives $$\left.\begin{aligned} D_{1,o} &= 0.7 \cdot \frac{5}{5+2} 60 Gy = 30 Gy \\ D_{2,o} &= 0.7 \cdot \frac{2}{5+2} 60 Gy = 12 Gy \end{aligned}\right\} = 42 Gy = 0.7 \cdot 60 Gy \right\} = D_{pr}$$
$$D_{3,o} = 0.3 \cdot \frac{1}{1} 60 Gy = 18 Gy$$

$$\left.\begin{aligned} D_{1,r} &= 0.2 \cdot \frac{5}{5+2} 60 Gy = 8.6 Gy \\ D_{2,r} &= 0.2 \cdot \frac{2}{5+2} 60 Gy = 3.4 Gy \end{aligned}\right\} = 12 Gy = 0.2 \cdot 60 Gy \right\} = D_{pr}.$$
$$D_{3,r} = 0.8 \cdot \frac{1}{1} 60 Gy = 48 Gy$$

In Equation 2, $c_{sp}=1$ was set, since no split plane is present.

On the basis of these equations, it is provided that at every point inside the target volume 4, the same total radiation dose is applied (e.g., in the exemplary embodiment from FIG. 11, $D_{pr}=60$ Gray). At the same time, the relative beam weights (e.g., $w_1=5$, $w_2=2$ and $w_3=3$ of the beams 3a to 3c) are maintained. For example, the ratio of 8.6 Gray to 3.4 Gray (e.g., the part radiation doses of the beams 3a and 3b in the sub-volume facing the rear side of the patch plane) is described by a ratio of 5:2 in accordance with the beam weights.

Figure 12:
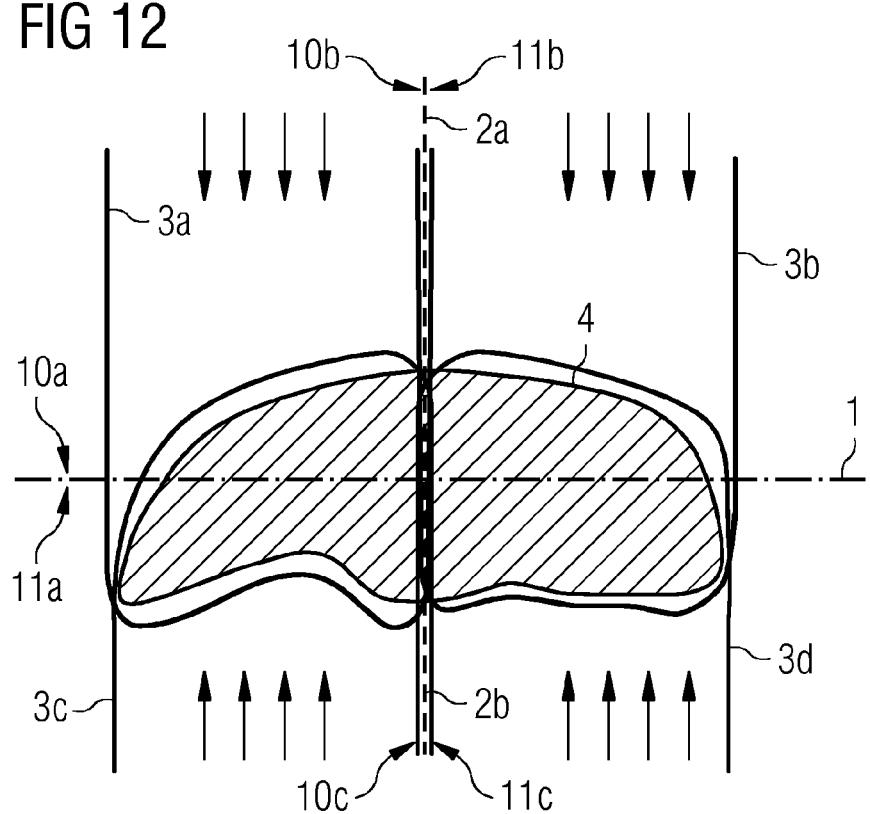
FIG. 12 illustrates an exemplary allocation of two beams to a patch plane, where the two beams are in each case divided in two by a split plane, such that a total of four beams are obtained.

With reference to FIG. 12, an example is represented, in which both a patch plane 1 and two split planes 2a and 2b are present. The patch plane 1 has a front side 10 that, in FIG. 12, is oriented upwards, and a rear side 1 that, in FIG. 12, is oriented downwards. Allocated to the front side 10 of the patch plane 1 are the beams 3a and 3b, while the beams 3c and 3d are allocated to the rear side 11 of the patch plane 1. The beams 3a and 3b are incident on the target volume 4 from a direction that differs from the direction of the beams 3c and 3d.

An application situation represented in FIG. 12 may, for example, be that the target volume 4 has too large an expansion, such that a single beam that is intended, for example, to be incident on the target volume 4 from the direction of the beams 3a and 3b may not cover the entire target volume 4. Possible reasons for this are that hardware limitations do not allow for the diameter of a beam to be selected as sufficiently large for the target volume 4 to be encompassed all at once. It is then provided for two beams (e.g., beams 3a and 3b in FIG. 12) that are linked to each other by a split plane (e.g., split plane 2a in FIG. 12) is described. The beam 3a is allocated to the front side 10b of the split plane 2a, and the beam 3b is allocated to the rear side 11b of the split plane 2a. The same applies accordingly to the beams 3c and 3d with reference to the split plane 2b.

Making use of the foregoing Equation 2, the part radiation doses of the different beams may be calculated. A numerical example is again represented to provide better illustration. In this situation, a dose fraction of $F_o=60\%$ is allocated to the patch plane 1, with reference to the front side, and a dose fraction of $F_r=80\%$ is allocated with reference to the rear side. These dose fractions have already been discussed in detail with reference, for example, to the foregoing FIG. 11. The radiation weighting factors for the different beams are: for beam 3a $w_{1.1}=1$; for beam 3b: $w_{1.2}=2$; for beam 3c: $w_{2.1}=3$; for beam 3d: $w_{2.2}=4$. In this situation, the doubled indices also indicate the allocation to one of the split planes 2a and 2b. The calculation of the part radiation doses then provides, for the different beams:

$$\left.\begin{aligned} D_{1.1, area\ 1.1} &= \frac{1 \cdot 1}{1 \cdot 1 + 2 \cdot 0} \cdot 0.6 \cdot 60 Gy = 36 Gy \\ D_{1.2, area\ 1.1} &= 0 Gy \\ D_{2.1, area\ 1.1} &= \frac{3 \cdot 1}{3 \cdot 1 + 4 \cdot 0} \cdot 0.4 \cdot 60 Gy = 24 Gy \\ D_{2.2, area\ 1.1} &= 0 Gy \end{aligned}\right\} = 60 Gy = D_{pr}.$$

Once again, the choice of the different numerical factors is purely by way of example, and different numerical factors may be chosen.

In the example from FIG. 12, the position of the split planes along the patch plane is identical: This provides that the position of the split plane 2a is the same as the position of the split plane 2b in relation to the patch plane 1. This allows for a simple calculation with the foregoing Equation 2, since the different local weighting factors for the different beams at the same points along the patch plane are equal to 1 or equal to 0, respectively.

Figure 13:
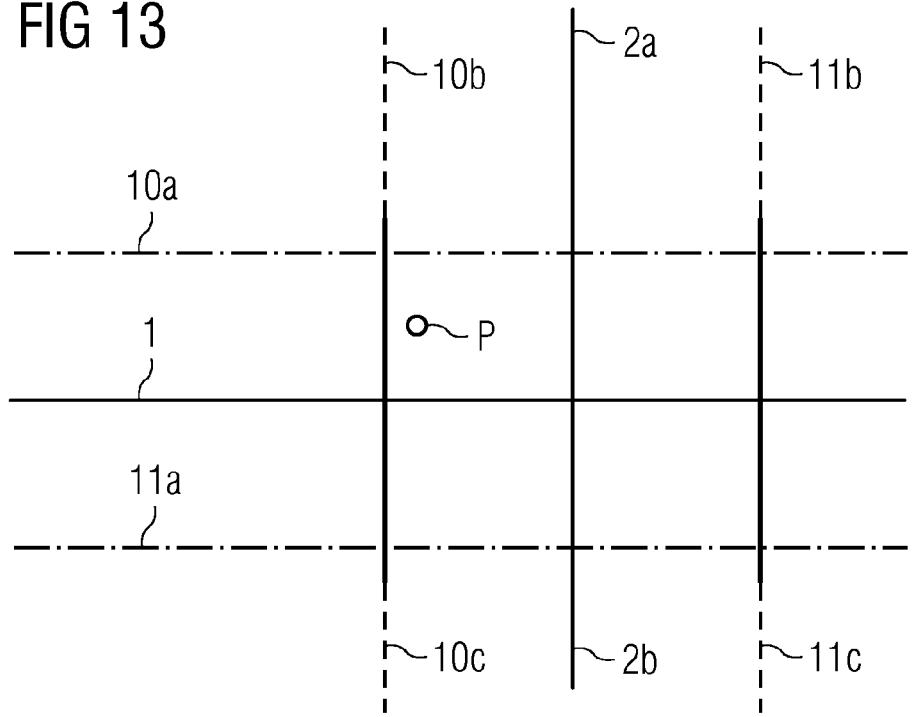
FIG. 13 illustrates an exemplary calculation of the local part radiation dose inside a patch plane and inside a split plane.

FIG. 13 is an enlargement of a section from FIG. 12. For example, the section, in which the patch plane 1 intersects with the split planes 2a and 2b, is enlarged. In FIG. 13, the split planes 2a and 2b run in a vertical direction, and the patch plane 1 runs in a horizontal direction. In each case, the front and rear sides of the different split planes and patch planes are represented. The front side 10a of the patch plane and the rear side 11a of the patch plane 1 are represented by a broken line. The front sides of the split planes 2a and 2b are identified by the reference numbers 10b and 10c. The rear sides of the split planes 2a and 2b are identified by the reference numbers 11b and 11c.

The part radiation doses for the different beams are calculated for the point P. From FIG. 12, four beams 3a to 3d (not shown in FIG. 13) contribute to the dose. Inside the different planes, inside the patch plane 1 and inside the split planes 2a and 2b, a linear dose gradient is to be applied. Subject to this precondition and to the fact that the split planes 2a, 2b are located at the same position, the following is derived for the position of the point P:

$$c_{sp,3a} = c_{sp,3c} = 0.9 \rightarrow c_{sp,3b} = c_{sp,3d} = 0.1$$

$$c_{pp,3a} = c_{pp,3c} = 0.55 \rightarrow c_{pp,3b} = c_{pp,3d} = 0.45.$$

In the following two equations, the indices 3a-3d indicate the beams 3a-3d. With the foregoing equation, the dose of the different beams may be calculated. The factors $c_{sp}$ and $c_{pp}$ are derived by linear scaling according to the position of the point P and of the thickness of the split planes and patch planes. This again takes place in isolation for the front side 10a and the rear side 11a of the patch plane 1 in each case. For the front side 10a of the patch plane 1, the dose contributions are derived at the point P of the beams 3a and 3b in the transition area as:

$$D_{3a,trans} = \frac{1 \cdot 0.9}{1 \cdot 0.9 + 2 \cdot 0.1} \cdot 0.55 \cdot 60 Gy = 27 Gy$$

$$D_{3b,trans} = \frac{2 \cdot 0.1}{1 \cdot 0.9 + 2 \cdot 0.1} \cdot 0.55 \cdot 60 Gy = 6 Gy.$$

For the rear side of the patch plane 1, the dose contributions at the point P of the beams 3c and 3d in the transition are derived accordingly as $$D_{3c,trans} = \frac{3 \cdot 0.9}{3 \cdot 0.9 + 4 \cdot 0.1} \cdot 0.45 \cdot 60 Gy = 23.5 Gy$$

$$D_{3d,trans} = \frac{4 \cdot 0.1}{3 \cdot 0.9 + 4 \cdot 0.1} \cdot 0.45 \cdot 60 Gy = 3.5 Gy.$$

As shown, the sum of the part radiation doses for the beams 3a to 3d gives the total radiation dose $D_{pr}$=60 Gray. At the same time, the beam weights are taken into account accordingly. The local weighting factors $c_{sp}$ and $c_{pp}$ again adopt a weighting of the local dose such that a gradual transition of the applied part radiation doses is provided.

Making reference once again to FIG. 12, a simple case will be illustrated. Equation 3 may be used for the calculation of the part radiation doses $D_i$ of the beams 3a to 3d in FIG. 12. The parameters (e.g., the dose fractions and the beam weights) are to be selected in accordance with the exemplary embodiment discussed in FIG. 12. Accordingly, by applying the formula referred to above, the following is derived:

$$\left. \begin{array}{l} D_{1.1,area\ 1.1} = \dfrac{1 \cdot 1 \cdot 0.6}{1 \cdot 1 \cdot 0.6 + 2 \cdot 0 \cdot 0.6 + 3 \cdot 1 \cdot 0.4 + 4 \cdot 0 \cdot 0.4} \cdot 60 Gy = 0.33 \cdot 60 Gy \\[6pt] D_{1.2,area\ 1.1} = 0 Gy \\[6pt] D_{2.1,area\ 1.1} = \dfrac{3 \cdot 1 \cdot 0.4}{1 \cdot 1 \cdot 0.6 + 2 \cdot 0 \cdot 0.6 + 3 \cdot 1 \cdot 0.4 + 4 \cdot 0 \cdot 0.4} \cdot 60 Gy = 0.66 \cdot 60 Gy \\[6pt] D_{2.2,area\ 1.1} = 0 Gy \end{array} \right\} = 60 Gy = D_{pr}.$$

The calculation in accordance with the formula above still provides the specified total radiation dose $D_{pr}$=60 Gy. However, the calculation reveals that the sub-volume part radiation doses that are allocated to the corresponding sub-volumes of the front side and rear side, respectively, of the patch plane has been changed from 60% to 33%. This change was not specified according to the radiation plan, in which a dose fraction of 60% was specified. Accordingly, the calculation according to Equation 2, as discussed heretofore in relation to the exemplary embodiment in FIG. 12, is better suited for the calculation of a part radiation dose for the different beams involved such that the total radiation dose is derived from the sum of the part radiation dose and, at the same time, the respective specified sub-volume total radiation doses are maintained.

With reference to FIG. 14, an example is described hereinafter in which a total of six beams 3a-3f are linked to a patch plane. The front side 10a of the patch plane 1 and the rear side 11a are indicated. Four split planes 2a, 2b, 2c, 2d also exist. The front sides of the split planes 2a, 2b, 2c, 2d are indicated by 10b-10e, and the rear sides correspondingly are indicated by 11b-11e. In this situation, the beams 3a and 3b are linked to split plane 2c, the beams 3b and 3c are linked to split plane 2d, the beams 3d and 3e are linked to split plane 2a, and the beams 3e and 3f are linked to split plane 2b. A seventh beam 3g is not linked to any of these control planes 1, 2a, 2b, 2c, 2d.

This example illustrates the presence of several local weighting factors $c_{sp}$. The use of beam weights $w_i$ for beams with and without allocation to control planes is illustrated. The numerical examples are purely illustrative and not restrictive. Other parameters may also be selected depending on the application situation.

The beam weights of the beams 3a-3c (in FIG. 14 from the top):

$$w_1 = w_2 = w_3 = 3,$$

where, here and in the following explanations for FIG. 14, the indices 1-7 designate the beams 3a-3g.

The beam weights of the beams 3d-3f (in FIG. 14 from the bottom):

$$w_4 = w_5 = w_6 = 4.$$

For the calculation of the corrected total radiation dose $D_{pr}$*, a weight is allocated to the patch plane that is used for the calculation of the part radiation dose $D_7$ of the beam 3g:

$$w_{pp} = 2.$$

Accordingly, the weight of the beam 3g without allocation to the patch plane 1:

$$w_7 = 1.$$

The local weighting factors of the patch plane 1:

$$c_{pp,1} = 0.7; c_{pp,2} = 0.8.$$

The total radiation dose $D_{pr}$=60 Gy.

The part radiation dose of the beam $3g$ is then calculated as:

$$D_7 = \frac{1}{1+2} 60 Gy = 20 Gy$$

This provides that the sum of the part radiation doses of all the beams linked to patch planes amounts to $D_{pr}{}^* = 40$ Gy.

Based on this, the calculation of the part radiation doses may be carried out for the different beams $3a$-$3f$, and specifically for the point P, as is indicated in FIG. 14. Point P is located in FIG. 14 beneath the patch plane inside the split plane $2b$. By way of example, with reference to this position, the following two local weighting factors are used: Beam $3b$: $c_{sp,2}$=0.6; Beam $3c$: $c_{sp,3}$=0.4; Beam $3a$: $c_{sp,1}$=0; Beam $3e$: $c_{sp,5}$=0.3; Beam $3f$: $c_{sp,6}$=0.7; Beam $3d$: $c_{sp,4}$=0.

Beam $3b$:

$$D_2 = \frac{3(1 \cdot 0,6)}{3(1 \cdot 0,6) + 3(1 \cdot 0,4)} \cdot 0,2 \cdot 40 Gy = 4,8 Gy.$$

Beam $3c$:

$$D_3 = \frac{3(1 \cdot 0,4)}{3(1 \cdot 0,6) + 3(1 \cdot 0,4)} \cdot 0,2 \cdot 40 Gy = 3,2 Gy.$$

Beam $3a$:

$D_1$=0.

Beam $3e$:

$$D_5 = \frac{4(1 \cdot 0,3)}{4(1 \cdot 0,3) + 4(1 \cdot 0,7)} \cdot 0,8 \cdot 40 Gy = 9,6 Gy.$$

Beam $3f$:

$$D_6 = \frac{4(1 \cdot 0,7)}{4(1 \cdot 0,3) + 4(1 \cdot 0,7)} \cdot 0,8 \cdot 40 Gy = 22,4 Gy.$$

Beam $3d$:

$D_4$=0.

The sum of the part radiation doses of the beams $3a$-$3f$ again amounts to 40 Gy.

With reference to FIG. 15, acts used in order to carry out a spatially-resolved calculation of the part radiation dose $D_i$ are shown. The method begins with act S0. In act S1, a total radiation dose $D_{pr}$ is defined. For example, the total radiation dose may be defined on the basis of a specified dose from a radiation plan. The prescribed dose may be selected on the basis of clinical aspects. In act S2, the definition of a target volume is carried out. The target volume may, for example, be a tumor. The target volume may, for example, be determined on the basis of three-dimensional image data sets, obtained, for example, by magnetic resonance tomography or computed tomography imaging methods.

In act S3, the determination of a first control plane takes place. The first control plane corresponds to a patch plane. The first control plane may be deposited geometrically into the target volume by suitable techniques, inside the three-dimensional image data set.

In act S4, assigned to the first control plane determined in act S3 is a dose fraction $F_o$ and $F_r$, respectively, that designates the fraction of the sub-volume total radiation dose in the total radiation dose for all the beams linked to one side of the first control plane. The sub-volume total radiation dose designates the dose that is applied in the sub-volume that faces a side of the first control plane by all the beams linked to this side. This has been described in relation to FIG. 2.

A first control plane determined in act S3 exhibits, for example, a certain thickness. The position of the first control plane may be described, for example, by the mid-point of the control plane, and the control plane is further characterized by a front side and a rear side. For example, beams linked to the control plane may allow for a gradual transition of the part radiation dose as a function of the location inside the first control plane. This takes place by a spatially-resolved determination of the first local weighting factors cpp. The first local weighting factors are allocated respectively to a first control plane and, respectively, to a side of the first control plane. This has been discussed in relation to FIG. 2.

In act S5, a beam is determined, and the respective beam is linked or allocated to a side of the patch plane. A beam is in each case allocated unambiguously to a side of a patch plane. A beam may not, for example, be linked to several sides of different patch planes or of the same patch plane. In act S6, a check is carried out as to whether a further beam is necessary. For example, there may be dosimetric reasons for using several beams for the application of the total radiation dose $D_{pr}$ inside the target volume. This has been described heretofore. If it is determined in act S6 that a further beam is necessary, then act S5 may be repeated, and the further beam is determined.

If, however, it is determined in act S6 that no further beam is necessary, then in act S7, a check is carried out as to whether a further patch plane is necessary. If this is the case, acts S3-S6 are repeated. If, however, it is determined that no further patch plane is needed, then the method continues with S8. In act S8, a check is carried out for each act as to whether a splitting of the beam is necessary. For example, a splitting of a beam into several beams may be necessary due to hardware-induced limitations. If, for example, a laminated collimator is used to focus the beams, then this laminated collimator may have a limited field of vision. However, if the size of the beam, which was determined in act S5, is greater than this maximum field of vision, then a splitting of the beam is provided, and act S8 follows act S9.

In act S9, a second control plane (e.g., a split plane) is determined for the respective beam. Several split planes may also be determined. As has been described heretofore with reference to FIG. 3, there are a number of possibilities for calculating the position and the number of the split planes to be provided with a given beam size. These calculations may be drawn on in act S9 for the determination of the split plane. In act S10, the splitting of the beam takes place into several beams (e.g., two beams), and the beams obtained in this way are linked with the respective split plane.

The original beam is then no longer relevant to the further processing. For example, from one beam, by definition of a split plane, two beams are used that then physically apply dose at a later point in time. The original beam, which was determined, for example, in act S5, is a purely virtual beam that is used in the course of the calculation presently being discussed. The virtual does not have any physical effect, however, on the irradiation process, for example.

In act S11, second local weighting factors $c_{sp}$ are determined for each beam. The second local weighting factors allow for a spatially-resolved calculation of the part radiation doses for the different beams with reference to the positioning in relation to second control planes.

In act S11, whether a further beam is present is determined. If a further beam is present, then act S8 is carried out again (e.g., a check is again made with regard to the beam that is now selected as to whether splitting into several beams is necessary). If it is determined in act S8, that no splitting is necessary, then acts S9-S11 are omitted. Otherwise, acts S9 and S11 are carried out again.

With regard to beams that are linked to second control planes (e.g., split planes), a beam may also be allocated, for example, to two or more second control planes. This has been explained with reference to FIG. 5. This represents a difference between the linking of beams to second control planes, as takes place in act S10 and the linking of beams to first control planes, as takes place in act S5.

If it is determined in act S12 that no further beam is present, then act S13 follows. Act S13 is an optional act. In act S13, beams that have no allocation to a first control plane (e.g., a patch plane) may be determined. Such beams apply a part beam dose (e.g., homogeneous) over the entire target volume that was determined in act S2. Following this, in act S14, beam weights $w_i$ are determined for all beams (e.g., for beams that are linked to a first or second control plane) as well as for beams that do not exhibit such a linking. Such beam weights $w_i$ have been discussed in relation to FIGS. 10-14. The beam weights $w_i$ allow for a relative weighting of the part radiation doses of different beams in relation to one another. The use of part radiation doses may allow for an optimization from dosimetric points of view.

In act S15, the part radiation doses $D_i$ for each beam that does not exhibit any linking to a first or second control plane are calculated. For example, this calculation has been described in relation to FIG. 10. The sum of the part radiation doses $D_i$ of those beams that do not exhibit any linking to a first or second control plane is used in order for a corrected total radiation dose $D_{pr}^*$ to be assigned in act S16. This corrected total radiation dose is used in act S17 and following acts for the calculation of the part radiation doses of the linked beams.

This calculation starts in act S17, in that a patch plane is selected in each case. In acts S18 and S19, separately for, respectively, the front side and the rear side of the selected patch plane, the calculation of the part radiation dose $D_i$ for the beams that are linked to the just selected front side and rear side, respectively, of the patch plane. In act S18, the part beam dose $D_i$ is calculated in isolation for all beams that are linked to the front side of the selected patch plane. This calculation is carried out on the basis of the first and second local weighting factors $c_{sp}$ and $c_{pp}$, as well as the corrected total radiation dose $D_{pr}^*$ as obtained from act S16. If act S13 does not take place (e.g., no beams exist without a link to first or second control planes), then the corrected total radiation dose $D_{pr}^*$ is equal to the total radiation dose $D_{pr}$ as was determined in act S1. In act S19, the corresponding calculation for all beams that are linked to the rear side of the selected patch plane takes place.

In act S20, a check is carried out as to whether further planes are present. If further patch planes are present, the acts S17-S19 are again carried out. Otherwise, all part radiation doses of the different beams are calculated, and it is possible in act S21 for an irradiation of the target volume to be carried out in accordance with the calculated parameters of the different beams. The method then comes to an end in act S22.

The sequence of the acts, as has been discussed in relation to FIG. 15, is variable. For example, act S13 (e.g., the determination of beams without allocation to patch planes) may be carried out before, for example, act S3 (e.g., before the determination of beams with allocation to patch planes). The beams may be linked to split planes (acts S8-S12), and the split beams may be allocated to patch planes (acts S3-S7).

Although the invention has been illustrated and described in detail by the exemplary embodiments, the invention is not restricted by the examples disclosed, and other variations may be derived from these by the person skilled in the art without departing from the scope of protection of the invention.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for calculating local part radiation doses in a radiotherapy system for the application of a total radiation dose in a target volume with beams, the method comprising:
   determining, by a treatment planning system, a location of at least one first control plane for controlling the dosing of the beams, wherein each of the at least one first control plane divides the target volume into two part volumes;
   allocating, by the treatment planning system, at least one of the beams for a front side and a rear side of each of the at least one first control plane, respectively;
   determining, by the treatment planning system, for each of the at least one first control plane, a sub-volume total radiation dose for each of the two part volumes as a fraction of the total radiation dose;
   determining, by the treatment planning system, a location of at least one second control plane for the control of the positioning of the beams, wherein each of the at least one second control plane divides the target volume into two sub-volumes;
   allocating, by the treatment planning system, at least one of the beams to each of the at least one second control plane, wherein the at least one beam allocated to the second control plane is divided in two by the respective second control plane such that a local part radiation dose of two beams obtained in this way in different sub-volumes, defined by the respective second control plane, is not equal to zero;
   calculating, by a processing device, for at least one side of the at least one first control plane, in isolation, the corresponding local part radiation doses of all the beams allocated to the at least one first control plane, such that the sum of the local part radiation doses of the beams that are allocated to the side of the respective first control plane that faces the respective sub-volume, provides the respective sub-volume total radiation dose, and the sum of the local part radiation doses of the beams allocated to the remainder of the at least one first control plane provides a difference between the respective sub-volume total radiation dose and the total radiation dose; and
   applying, by a radiation generating device, said beams based on the local part radiation doses calculated by the processing device.

2. The method as claimed in claim 1, wherein allocating the at least one beam for the front side and the rear side of each of the at least one first control plane comprises allocating a beam in each case to a side of the at least one first control plane.

3. The method as claimed in claim 1, wherein the local part radiation doses of a beam allocated to a side of a first control plane of the at least one first control plane are different in the sub-volumes defined by the first control plane.

4. The method as claimed in claim 1, wherein the at least one first control plane includes a finite thickness, and wherein beams that exhibit different local part radiation doses on different sides of a respective first control plane of the at least one first control plane provide, by a local course of the local part radiation dose inside the respective first control plane, a gradual transition of the local part radiation dose.

5. The method as claimed in claim 1, further comprising determining a beam weight for each of the beams, wherein the beam weights determine relative ratios of the part radiation doses of different beams to one another.

6. The method as claimed in claim 5, wherein also inside the target volume for a specific side of a specific first control plane of the at least one first control plane, the method further comprises:

determining first local weighting factors for each distance interval perpendicular to the specific first control plane, wherein the first local weighting factors define fractions of the sub-volume total radiation dose in the total radiation dose;

determining, for each of the beams allocated to the specific side of the specific first control plane, second local weighting factors for each distance interval perpendicular to a second control plane, to which the respective beam is allocated, wherein the second local weighting factors modify the beam weights of the beams as a function of a position in relation to the at least one second control plane; and calculating, for each of the beams allocated to the specific side of the specific first control plane, the local part radiation dose for each sub-volume for the respective beam based on elements, the elements comprising radiation weighting factors, the first local weighting factors, the second local weighting factors, the total radiation dose, or a combination thereof.

7. The method as claimed in claim 6, wherein, in the calculation of the local part radiation dose, the second local weighting factors modify the radiation weighting factors between 0% and 100% of the radiation weighting factors.

8. The method as claimed in claim 6, wherein the at least one first control plane and the at least one second control plane include a thickness, the first local weighting factors and the second local weighting factors varying inside a corresponding control plane of the at least one first control plane and the at least one second control plane as a function of a position.

9. The method as claimed in claim 5, wherein the calculation of the local part radiation dose is carried out in a spatially-resolved manner in accordance with the following formula for one side of a first control plane of the at least one control plane $$D_i = \frac{w_i \prod_k c_{sp,i,k}}{\sum_{j=1}^{n} w_j \prod_l c_{sp,j,l}} c_{pp} D_{pr},$$

wherein $w_i$ designates the radiation weighting factors, $c_{pp}$ designates the corresponding spatially-resolved first local weighting factor, $c_{pp}D_{pr}$ designates the sub-volume total radiation dose, $D_{pr}$ designates the total radiation dose, k and l are indices, and $c_{sp}$ designates the spatially-resolved second local weighting factors for all beams that are allocated to the corresponding side of the first control plane.

10. The method as claimed in claim 1, further comprising determining beams without allocation to first control planes or second control planes, wherein the part radiation doses of the beams without allocation are deducted before the calculation in isolation of the total radiation dose.

11. The method as claimed in claim 10, further comprising:

determining radiation weighting factors for the beams without allocation to a first control plane of the at least one first control plane or a second control plane of the at least one second control plane; and adjusting the total radiation dose for beams that are allocated to the first control plane, the second control plane, or the first control plane and the second control, based on radiation weighting factors for the beams without allocation to the first control plane or the second control plane.

12. The method of claim 1, further comprising:

defining the total radiation dose based on a predetermined dose of a radiation plan; and defining the target volume based on a three-dimensional image data set.

13. The method of claim 12, further comprising geometrically depositing the at least one first control plane into the target volume, inside the three-dimensional image data set.

14. The method of claim 13, wherein a position of a first control plane of the at least one deposited first control plane is identified by a midpoint of the first control plane.

15. The method of claim 1, wherein the front side and the rear side of a first control plane of the at least one first control plane is perpendicular to a path of at least one of the beams.

16. A method for the calculation of local part radiation doses in a radiotherapy system, for the application of a total radiation dose in a target volume with beams, the method comprising:

determining, by a treatment planning system, a location of at least one control plane for the controlling of the positioning of the beams, wherein each of the at least one control plane divides the target volume into two sub-volumes;

allocating, by the treatment planning system, at least one of the beams to each of the at least one control plane, wherein a beam allocated to the at least one control plane is divided in two by the respective control plane such that the local part radiation dose of two of the beams obtained in this way in each case in different sub-volumes, defined by the respective control plane, is not equal to zero;

determining beams without allocation to at least one control plane or at least one other control plane;

correcting the total radiation dose by subtraction of the local part radiation doses of the beams without allocation of the total radiation dose;

calculating the local part radiation doses for all beams allocated to a control plane of the at least one control plane, the calculating of the local part radiation doses comprising determining, by the treatment planning system, for the control plane a sub-volume total radiation dose for each of the two sub-volumes as a fraction of the total radiation doses; and applying, by a radiation generating device, said beams based on the local part radiation doses calculated by the treatment planning system.

17. The method as claimed in claim 16, further comprising determining, for each of the beams, a beam weight, wherein the beam weights determine relative ratios of the part radiation doses of different beams to one another.

18. The method as claimed in claim 17, wherein, for the correction of the total radiation dose, the beam weights of all the beams allocated to a control plane of the at least one control plane is in sum one.

19. The method as claimed in claim 16, wherein the sum of the local part radiation doses of all the beams at each position inside the target volume is equal to the total radiation dose.

20. The method as claimed in claim 16, wherein the at least one control plane includes a finite thickness, and
wherein beams that are divided in two by a control plane of the at least one control plane, by a local course of the local part radiation dose inside the control plane, provide a gradual transition of the local part radiation dose.

21. The method as claimed in claim 16, wherein the local part radiation dose for a beam allocated to a first control plane of the at least one other control plane is not equal to zero on different sides of the first control plane, and
wherein the local part radiation dose for a beam allocated to a second control plane of the at least one control plane on one of the sides of the control plane is equal to zero.

22. The method as claimed in claim 16, wherein the beams are characterized by a beam source, and
wherein the beam source designates a position, at which a beam is produced.

23. The method as claimed in claim 22, wherein two of the beams, which are divided in two by a control plane of the at least one control plane, have essentially the same beam sources.

24. The method as claimed in claim 16, further comprising determining the at least one control plane such that beams that exhibit a part radiation dose in the target volume that is greater than a maximum target volume accessible to the beam are divided in two by the at least one control plane.

25. The method as claimed in claim 16, wherein the at least one control plane designates patch planes of a radiation plan, and
wherein the at least one other control plane designates split planes of the radiation plan.

26. A radiotherapy system comprising:
a treatment planning system;
a processing device; and
a radiation generating device,
wherein the treatment planning system is configured, for the calculation of local part radiation doses for the application of a total radiation dose in a target volume with beams, to:
determine a location of at least one first control plane for the controlling of the dosing of beams, wherein each of the at least one first control plane divides the target volume into two sub-volumes;
allocate at least one of the beams for a front side and a rear side of each of the at least one first control plane, respectively;
determine a sub-volume total radiation dose for each of the two sub-volumes as a fraction of the total radiation dose, for each of the at least one first control plane;
determine a location of at least one second control plane for the controlling of the positioning of the beams, wherein each of the at least one second control plane divides the target volume into two sub-volumes; and
allocate at least one of the beams to each of the at least one second control plane,
wherein a beam allocated to a second control plane of the at least one second control plane is divided in two by the respective second control plane such that the local part radiation dose of two beams obtained in this way in different sub-volumes defined by the respective second control plane is not equal to zero,
wherein the processing device is configured to, for at least one side of a first control plane of the at least one first control plane, calculate, in isolation, the corresponding local part radiation doses of all the beams allocated to the first control plane, such that a sum of the local part radiation doses of the beams that are allocated to the at least one side of the first control plane facing the respective sub-volume provides the respective sub-volume total radiation dose, and the sum of the local part radiation doses of the remaining beams allocated to the first control plane provides a difference between the respective sub-volume total radiation dose and the total radiation dose, and
wherein the radiation generating device is configured to apply beams with the local part radiation doses calculated by the processing device.

27. The radiotherapy system as claimed in claim 26, wherein the local part radiation doses of a beam allocated to a side of a first control plane of the at least one first control plane are different in the sub-volumes defined by the first control plane.

28. A radiotherapy system comprising:
a treatment planning system;
a processing device; and
a radiation generating device, wherein the treatment planning system is configured, for calculating local part radiation doses for the application of a total radiation dose in a target volume with beams, to:
determine a location of at least one control plane for the controlling of the positioning of the beams, wherein each of the at least one control plane divides the target volume into two sub-volumes;
allocate at least one of the beams to each of the at least one control plane, wherein a beam allocated to a control plane of the at least one control plane is divided in two by the respective control plane such that the local part radiation dose of two beams obtained in this way in different sub-volumes, defined by the respective control plane, is not equal to zero,
wherein the treatment planning system is configured to determine beams without allocation to the at least one control plane or at least one other control plane, wherein the processing device is configured to:
  correct the total radiation dose by subtraction of the local part radiation doses of the beams without allocation of the total radiation dose; and
  calculate the local part radiation doses for all the beams allocated to a control plane of the at least one control plane, the calculation of the local part radiation doses comprising determination for the control plane a sub-volume total radiation dose for each of the two sub-volumes as a fraction of the total radiation dose, and
wherein the beam generating device is configured to apply beams with the local part radiation dose calculated by the processing device.

29. The radiotherapy system as claimed in claim 28, wherein the processing device is configured to determine, for each of the beams, a beam weight, and
  wherein the beam weights determine relative ratios of the part radiation doses of different beams to one another.

* * * * *